United States Patent [19]
Regan et al.

[11] Patent Number: 5,674,482
[45] Date of Patent: *Oct. 7, 1997

[54] POLYMERS WITH ALKYL- OR HETEROALKYL -ARYL BACKBONE AND PHARMACEUTICAL COMPOSITIONS INCORPORATING SAME

[75] Inventors: John R. Regan, Princeton, N.J.; Michael N. Chang, Newtown; Jack Newman, Warrington, both of Pa.; Schmuel Ben-Sasson, Jerusalem, Israel

[73] Assignee: Rhone-Poulenc Rorer Pharmaceuticals, Inc., Collegeville, Pa.

[*] Notice: The term of this patent shall not extend beyond the expiration date of Pat. No. 5,571,506.

[21] Appl. No.: 742,794

[22] Filed: Aug. 9, 1991

Related U.S. Application Data

[63] Continuation-in-part of PCT/US90/06847, Nov. 21, 1990, which is a continuation-in-part of Ser. No. 440,584, Nov. 22, 1989, abandoned, and Ser. No. 440,586, Nov. 22, 1989, abandoned, each is a continuation-in-part of Ser. No.393, 873, Aug. 14, 1989, abandoned.

[51] Int. Cl.$^6$ .................. A61K 31/775; C08G 8/04
[52] U.S. Cl. .................. 424/78.37; 528/148; 528/149; 528/150
[58] Field of Search .............. 424/78.08, 78.26, 424/78.37; 528/129, 181, 204, 206, 210, 218, 148–150; 525/450, 480, 508, 534

[56] References Cited

U.S. PATENT DOCUMENTS

| | | | |
|---|---|---|---|
| 1,344,950 | 6/1920 | Koetzle | 528/148 |
| 2,097,345 | 10/1937 | Rothrock | 528/148 |
| 2,323,481 | 7/1943 | McQueen | 528/148 |
| 2,910,484 | 10/1959 | de Stevens | 260/340.3 |
| 2,990,334 | 6/1961 | Graham | 424/456 |
| 3,025,260 | 3/1962 | Luck et al. | 260/43 |
| 3,035,022 | 5/1962 | Paris | 260/52 |
| 3,298,985 | 1/1967 | Bills et al. | 528/148 |
| 4,604,404 | 8/1986 | Munson, Jr. et al. | 514/494 |
| 4,617,336 | 10/1986 | Pastor et al. | 524/291 |
| 5,023,311 | 6/1991 | Kubota | 528/153 |

FOREIGN PATENT DOCUMENTS 0 354 714  2/1990  European Pat. Off. .

OTHER PUBLICATIONS

Merck Index, 10th Ed., 1983, pp. 312–313, #2182.
Smith et al., *J. Biol. Chem.*, 248(1), 122–130 (1973).
Smith et al., *Analytical Chemistry*, 21, No. 11, 1334 (1949).
Anderson et al., *Nature*, 332, 360–61 (1988).
Hakemalaki & Moshfegh, *Helvetica Chimica Acta*, 64, 599 (1981).
Vlodavsky et al., *Cancer Research*, 43, 2704–2711 (1983).
Nilsson–Ehle & Schotz, *J. Lipid Res.*, 17, 536–541 (1976).
Belfrage et al., *J. Lipid Res.*, 10, 341–344 (1969).
Eilat et al., *J. Immunology*, 133, 489–494 (1984).
Kramps et al., *Scand. J. Clin. Lab. Invest.*, 43, 427–432 (1983).

*Primary Examiner*—Edward J. Webman
*Attorney, Agent, or Firm*—Synnestvedt & Lechner

[57] ABSTRACT

A biologically active polymeric compound comprising an alkylaryl or heteroalkylaryl backbone having about 5 to about 50 repeating aromatic ring-containing units and which, according to the computer program marketed as SYBYL® version 5.2 running on a DEC VAX® 11/750 computer, is capable of forming a linear backbone having a helical secondary structure, and wherein the maximum diameter of the helical structure, as measured by the alkylaryl or heteroalkylaryl backbone, is less than 3 times greater than the maximum diameter of the aryl group of the alkylaryl or heteroalkylaryl backbone.

46 Claims, 2 Drawing Sheets

POLYMERS WITH ALKYL- OR HETEROALKYL -ARYL BACKBONE AND PHARMACEUTICAL COMPOSITIONS INCORPORATING SAME

CROSS-REFERENCE TO RELATED APPLICATIONS

This application is a continuation-in-part of international application PCT/US 90/06847, filed Nov. 21, 1990, which is a continuation-in-part of U.S. application Ser. Nos. 07/440,584 and 440,586, both filed Nov. 22, 1989, both now abandoned, which are continuation-in-part applications of U.S. application Ser. No. 07/393,873, filed Aug. 14, 1989, now abandoned.

The invention described in the aforementioned '873 application describes and claims pharmaceutical compositions containing a class of aromatic polymeric compounds and to the use of such compositions in pharmaceutical applications. The present application is concerned with a novel class of aromatic polymers and to their use in pharmaceutical applications, including applications of the type referred to in the aforementioned '873 application.

FIELD OF THE INVENTION

The present invention relates to: (A) methods of treatment involving the use of pharmaceutical compositions containing aromatic polymers, including alkylaryl or heteroalkylaryl polymers, which mimic the pharmacological activities of bioactive naturally occurring polymers including glycosaminoglycans, peptides, and polynucleic acids, and affect the distribution in tissue of biologically active peptides and proteins normally bound to glycosaminoglycans; (B) pharmaceutical compositions containing such polymers; (C) novel polymers for use in such compositions and treatments; and (D) the preparation of such polymers.

Glycosaminoglycans (GAG) are linear polysaccharides formed by characteristic repeating disaccharide units usually composed of a uronic acid and a hexosamine. The term "acid mucopolysaccharides," was used originally to designate hexosamine-rich acid polysaccharides extracted from connective tissue. In recent years, the term "glycosaminoglycans" has gained greater acceptance and is now used in place of mucopolysaccharides. The hexosamine can be glucosamine or galactosamine, and the uronic acid can be glucuronic or iduronic acid. Sulphate groups are found on all glycosaminoglycans apart from hyaluronic acid, and all of the sulphated glycosaminoglycans are covalently linked to protein forming different classes of proteoglycans. However, it would be an oversimplification to consider glycosaminoglycans to be simple repeat-unit polysaccharides, since considerable chemical and configurational variability can be superimposed upon the component sugars.

Among other functions it has been shown that the glycosaminoglycans serve also as a support which binds various bioactive peptides. This association is based on a non-covalent interaction since the bound protein can be readily released upon the addition of free glycosaminoglycans. Well known examples of such bound proteins include enzymes such as lipoprotein lipase (LPL) or growth-regulating peptides such as fibroblast growth factor (FGF). Another example of GAG-protein interaction is that of the enzyme heparinase which participates in cell-invasion processes. It has been demonstrated also that the commercially available glycosaminoglycan, heparin, inhibits the growth of vascular smooth muscle cells and the proliferation of kidney mesangial cells. The former cell type is involved in arteriosclerosis while the latter plays a role in glomerulosclerosis.

Heparin is known also to be involved in the release of lipoprotein lipase, the inhibition of heparanase and the release of fibroblast growth factor. The most common application of heparin is as an anticoagulant where heparin interacts with proteins which play a key role in hemostasis.

Glycosaminoglycans such as heparin are a major constituent participating in the composition of various biological structures such as basement membranes, connective tissues, cartilage and cell-surface glycocalyx. Connective tissues are responsible for providing and maintaining form in the body. Functioning in a mechanical role, they provide a matrix that serves to connect and bind the cells and organs and ultimately give support to the body. Unlike the other tissue types (epithelium, muscle and nerve) formed mainly by cells, the major constituent of connective tissue is its extracellular matrix, composed of protein fibers, an amorphous ground substance, and tissue fluid, the latter consisting primarily of bound water of solvation. Embedded within the extracellular matrix are the connective tissue cells.

In terms of structural composition, connective tissue can be subdivided into three classes of components: cells, fibers and ground substance. The wide variety of connective tissue types in the body represents modulations in the degree of expression of these three components.

The amorphous intercellular ground substance fills the space between cells and fibers of the connective tissue; it is viscous and acts as a lubricant and also as a barrier to the penetration of the tissues by foreign particles. Glycosaminoglycans and structural glycoproteins are the two principal classes of components comprising the ground substance.

Various disease states are characterized by the pathological hydrolysis of structural glycoproteins such as collagen, fibronectin and elastin. This hydrolysis can be mediated by the enzyme, elastase, which is possibly the most destructive enzyme in the body. The elastase produced by human neutrophil leukocytes (otherwise known as PMN or HNE or HLE) is believed to be involved in various diseases characterized by the destruction of structural proteins comprising the ground substance, including pulmonary emphysema, chronic bronchitis, cystic fibrosis, bronchiectasis, adult respiratory distress syndrome, atherosclerosis, arthritis, psoriasis, vasculitis, glomerulonephritis and consumption coagulopathies associated with gram-negative sepsis or leukemias.

The present invention is based on the discovery of a class of compounds exhibiting properties which mimic the action of glycosaminoglycans and which are capable of modulating biological systems containing complexes between bioactive peptides and/or proteins and glycosaminoglycans by competing with the binding interactions of glycosaminoglycans.

SUMMARY OF THE INVENTION

In accordance with the invention described and claimed in aforementioned application Ser. No. 07/393,873, there is provided a pharmaceutical composition comprising, in admixture with a pharmaceutically acceptable carrier, a therapeutically effective amount of an aromatic ring-containing polymeric compound, substantially free of monomer, and having properties which mimic the pharmacological activity of glycosaminoglycans and which are capable of competing with the binding thereof to bioactive peptides and/or proteins. Examples of such polymeric compounds include those having a molecular weight of about 2,000 to about 20,000 Daltons and in which each monomeric unit of the polyaromatic compound includes from 1 to about 10 aromatic rings, which may be substituted by electronegative substituents and/or negatively charged residues. Among the preferred compounds for use in the pharmaceutical compositions are those in which each monomeric unit contains between 3 and 10 aromatic rings, and particularly those in which the aromatic rings contain at least one substituent on at least two of the rings. Examples of such substituents are —NRR$_1$, —N=R, —OR, =O, —NO$_2$, —COOR, -halogen, —SO$_2$OR, —SO$_2$NHR, —OSO$_2$OR and —R, with R being C$_1$-C$_{12}$ alkyl or hydrogen and R$_1$ being lower alkyl, hydrogen, phenyl and substituted phenyl.

Underlying a further aspect of the present invention is the surprising and unexpected discovery that polymeric compounds according to the present invention are characterized as selective and potent inhibitors of the enzyme, elastase, which is produced by human polymorphonuclear neutrophils (PMN). Accordingly, another aspect of the present invention relates to pharmacological methods comprising the administration of a pharmaceutical composition comprising an effective elastase-inhibiting amount of a said polymeric compound to a human or other animal patient suffering from an elastase-mediated connective tissue degradation disorder.

Particularly-preferred compositions described in the '873 application comprise polymers of the aforementioned type and having the formula

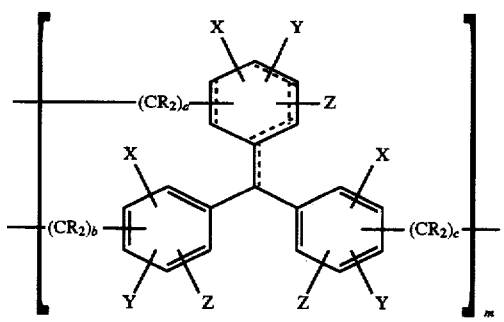

or a salt or ester thereof, wherein a, b and c are independently 0 or 1 and m is about 5 to about 20, and dashed lines represent optional single bonds, and each aromatic ring is substituted with at least one substituent (x, y, z) selected from —NRR$_1$, —N=R, —OR, =O, —NO$_2$, —COOR, -halogen, —SO$_2$OR, —SO$_2$NHR, —OSO$_2$OR and —R, wherein R is lower alkyl or hydrogen and R$_1$ is lower alkyl, hydrogen, phenyl or substituted phenyl.

The most preferred compositions described in the '873 application include compounds of the formula

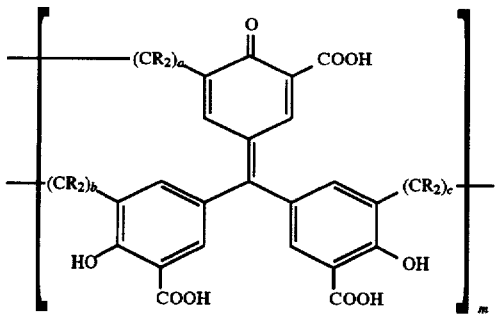

wherein R is as defined above, b and c are independently 0 or 1, a+b+c≧2 and m is about 5 to about 20.

The preferred molecular weight of the polymeric compounds which are the subject of the '873 application is described as being about 2,000 to about 20,000, the most preferred molecular weight being about 2,000 to about 4,000 Daltons, as measured by gel permeation chromatography.

Another aspect of the invention described and claimed in the aforementioned '873 application includes use of the aforementioned pharmaceutical compositions to treat humans or other animals for cardiovascular disorders, metabolic disorders of bone tissue, and neuronal disorders. Still another aspect of the invention described and claimed in the aforementioned '873 application comprises a method for effecting tissue redistribution of bioactive peptides and proteins which are normally bound to glycosaminoglycans comprising the administration of a pharmaceutical composition containing a tissue redistribution effective amount of a polymeric compound having a molecular weight of about 2,000 to about 20,000 Daltons and capable of mimicking the action of glycosaminoglycans in biological systems.

Aromatic polymers described in the aforementioned '873 application exhibit anticoagulant properties, are capable of being administered orally and are capable of being absorbed into the bloodstream from the gastrointestinal tract.

In accordance with the invention described and claimed in the present application, there is provided a biologically active polymeric compound having an alkylaryl or heteroalkylaryl backbone, including particularly those polymeric compounds having about 5 to about 50 repeating aromatic units. More specifically, there is included within the scope of the present invention a biologically active polymeric compound having an alkylaryl or heteroalkylaryl backbone and from about 5 to about 50 repeating aromatic ring-containing units and which, according to the computer program marketed as SYBYL® version 5.2 running on a DEC VAX® 11/750 computer, is capable of forming a linear backbone having a helical secondary structure, and wherein the maximum diameter of the helical structure, as measured by the alkylaryl or heteroalkylaryl backbone, is less than 3 times greater than the maximum diameter of the aryl group of the backbone. In preferred form, the polymeric compound is substantially linear. A preferred form of the invention includes polymeric compounds in which the alkylaryl or heteroalkylaryl group is polysubstituted, most preferably disubstituted or trisubstituted.

As described in detail below, one class of polymeric compounds of the present invention includes as a repeating unit in the polymeric chain a single mononuclear aromatic ring or a single polynuclear aromatic ring. Such polymeric compounds are prepared by polymerizing a monomeric form of a compound which comprises a mononuclear aromatic ring, for example, phenylenes such as hydroxybenzoic acid, or by polymerizing a monomeric form of a compound which comprises a polynuclear aromatic ring, for example, naphthalenes such as hydroxynaphthoic acid. Such compounds, that is, polymeric compounds prepared by polymerizing a monomeric form of the aromatic compound, are referred to herein as containing monomeric units, that is, the repeating aromatic ring-containing units are referred to as "monomeric units". As mentioned above, these polymers generally comprise from about 5 to about 50 repeating aromatic ring-containing units, i.e., about 5 to about 50 repeating monomeric units.

Another class of substantially linear polymeric compounds of the aforementioned type, that is, those which have the computer-predicted helical secondary structure referred to above, comprise polymeric compounds which include as a repeating unit in the polymeric chain two substituted aromatic rings, each of the aromatic rings being substituted with the same group(s) and being bonded together by an alkyl or heteroalkyl bridge. Preferably, the positions of the corresponding substituents of each ring have the same orientation (for example, ortho-, meta- or para-) with regard to the position of the bridge. The most preferred compounds are those which comprise as the repeating unit in the polymeric chain two identically-substituted phenylene groups and wherein the bridging groups are attached to each phenylene in an orientation meta- to each other.

Such polymeric compounds can be prepared by forming first the dimer of the monomeric form of the compound comprising the aromatic ring and then polymerizing the dimer. Alternatively, such polymeric compounds can be prepared by a sequential series of dimerization reactions, starting with the monomeric form of the compound comprising the aromatic ring and proceeding on to form, respectively, dimers, tetramers, octomers, etc. Such compounds are referred to herein as containing dimeric units, that is, the repeating aromatic ring-containing units are referred to as "dimeric units" or "dimers". As with the polymers prepared from monomeric units, these polymers generally comprise from about 5 to about 50 aromatic ring-containing units, i.e., about 3 to about 25 repeating dimeric units.

Still another class of substantially linear polymeric compounds of the aforementioned type, that is, those which have the computer-predicted helical secondary structure as referred to above, comprise polymeric compounds which include as a repeating unit in the polymeric chain three or more substituted aromatic rings, each of the aromatic rings being substituted with the same group(s) and being bonded together by an alkyl or heteroalkyl bridge. The most preferred compounds are those which comprise as the repeating unit in the polymeric chain three or more identically-substituted phenylene groups and wherein the bridging groups are attached to each phenylene in an orientation meta- to each other.

Such polymeric compounds can be prepared by forming first the multimer, e.g., trimers or tetramers, of the monomeric form of the compound comprising the aromatic ring and then polymerizing the multimer. It should be appreciated that, with regard to the use of such multimers, a simple dimerization of the multimer will suffice to produce a polymer according to the present invention, as the resulting compound would necessarily have at least six repeating aryl groups. These polymeric compounds are referred to herein as containing multimeric units, that is, the repeating aromatic ring-containing units are referred to as "multimeric units" or "multimers". Preferred multimers are trimers and tetramers, and it is expected that multimers up to and including octomers will be useful in the practice of the present invention. As discussed above, these polymers generally comprise from about 5 to about 50 aromatic ring-containing units, i.e., about 2 to about 16 trimeric units, about 2 to about 12 repeating tetrameric units, etc. As with the use of dimers discussed above, the multimers can be subjected to a series of sequential dimerizations, allowing the formation of polymers having specific degrees of polymerization.

The invention relates also to a pharmaceutical composition comprising, in admixture with a pharmaceutically acceptable carrier, a pharmaceutically-effective amount of a polymeric compound(s) within the scope of the present invention.

In accordance with another aspect of the present invention, polymeric compounds of the present invention are prepared by forming first the dimer or multimer of the monomeric form of the compound comprising the substituted aromatic ring and then polymerizing the dimer or multimer.

In accordance with another aspect of the present invention, polymeric compounds of the present invention are prepared by forming first the dimer or multimer of the monomeric form of the compound comprising the substituted aromatic ring and then by subjecting the dimer or multimer thus produced to one or more sequential dimerizations.

Pharmaceutical compositions within the scope of the present invention can include a single polymeric compound within the scope of the present invention or a mixture of such polymeric compounds. A mixture of such compounds can be produced conveniently by polymerization of appropriate monomers, dimers or multimers. Accordingly, another aspect of the present invention comprises a mixture of polymeric compounds produced by reacting lower alkyl aldehydes with substituted hydroxyaryls in the presence of an acid catalyst.

Still another aspect of the present invention relates to pharmacological methods comprising the administration of an effective amount of the above mentioned pharmaceutical composition to human or other animal patients in need of cardiovascular therapy such as anticoagulant and/or antithrombotic therapy and/or bone metabolic therapy and/or therapy for the treatment of neuronal disorders and/or gastrointestinal disorders and/or disorders which may be treated by agents effective in binding DNA.

Polymeric compounds within the scope of the present invention include compounds which have properties which mimic the pharmacological activity of glycosaminoglycans and are capable of competing with the binding thereof to bioactive peptides and/or proteins.

With regard to the helical structure of the polymers of the present invention, it is theorized that polymerization of dimers and multimers can result in a polymer having a more regular repeating structure than those formed directly from monomers. It is believed that such increased regularity aids in the formation of the helical secondary structure. As the bioactivity of virtually all substances is determined, at least in pad, by steric considerations such as helical structure, it is believed that the helical regularity of the compounds of the present invention may reasonably be expected to affect their bioactivity.

Some advantages which flow from the practice of the present invention include extended duration of bioactivity in vivo, as compared to naturally occurring compounds such as heparin, and the availability of oral administration. Heparin, for example, cannot be administered orally, as it is degraded in the digestive system before being absorbed into the bloodstream. In practice, however, it is anticipated that the preferred mode of administration of the compounds of the present invention will be parenteral, for example, intravenous injection.

DETAILED DESCRIPTION OF THE INVENTION

Figure 1:
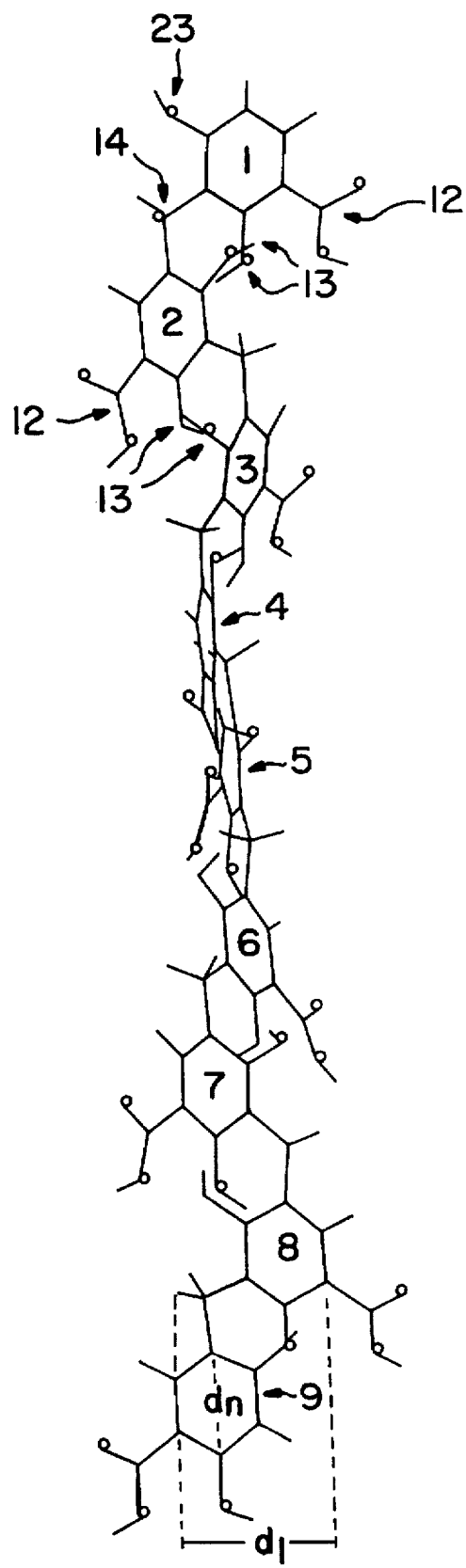
FIG. 1 is representative of a computer print of the structure of a polymer of the present invention, as predicted by the aforementioned computer program, viewed in a plane parallel to the helical axis of the polymer.

As employed above and throughout the disclosure, the following terms, unless otherwise indicated, shall be understood to have the following meanings.

"Distribution in tissue" and "tissue distribution" are used herein to mean either the compartmentalization of a molecular constituent within a given tissue or the distribution pattern between different tissues.

"Tissue redistribution" means a change in the compartmentalization within a given tissue or a change in the distribution pattern between tissues. For example, a peptide may be released from a basement membrane which can result subsequently in its consumption by surrounding cells or its transfer into the bloodstream, or a soluble compound could be bound to a protein in a competitive binding situation thereby preventing the association of said compound with certain tissue-fixed residues.

"Alkyl" means a saturated aliphatic hydrocarbon which may be either straight or branched-chained containing 1 to about 12 carbon atoms.

"Heteroalkyl", used herein with reference to the bridging group between the repeating aryl units of the present polymers, means an alkyl group wherein at least one carbon atom of the otherwise alkylaryl backbone is replaced with a heteroatom, for example, O, S or N. An exemplary heteroalkyl bridging group is methoxy, i.e., —OCH$_2$—.

"Lower alkyl" means an alkyl group as above, having 1 to about 4 carbon atoms.

"Alkyl aldehyde" means an aldehyde derived from an alkyl group, including, for example, formaldehyde.

"Aryl" means a 5 to 7-membered unsaturated mono- or di-aromatic cyclic organic group which can be homocyclic or heterocyclic, and which can be either mononuclear (single ring) or polynuclear (fused rings).

"Substituted phenyl" means a phenyl group substituted with one or more substituents which may be alkyl, alkoxy, amino, acetyl, nitro, carboxy, carboalkoxy, cyano, alkylamino, halo, hydroxy, hydroxyalkyl, mercaptyl, alkyl mercaptyl, phosphate, sulfate, carboalkyl or carbamoyl.

"Multimer" means any repeating unit of a polymer of the present invention which itself comprises at least three repeating aryl groups.

Certain of the polymeric compounds of the present invention may undergo keto-enal tautomerism, and all of these forms are considered to be included within the scope of this invention.

Polymeric compounds included in the compositions of this invention may be useful in the form of free bases and free acids, and also in the form of salts, esters and as hydrates. All forms are within the scope of the invention. Acid and base addition salts may be formed and are simply a more convenient form for use; in practice, use of the salt form inherently amounts to use of the base or acid form. The acids and bases which can be used to prepare the addition salts include preferably those which produce, when combined with the free base or acid, pharmaceutically acceptable salts, that is, salts whose ions are non-toxic to the animal organism in pharmaceutical doses of the salts, so that the beneficial pharmacological properties inherent in the free base or acid are not vitiated by side effects ascribable to the ions. Although pharmaceutically acceptable salts of said compound are preferred, all addition salts are useful as sources of the free base or acid form even if the particular salt per se is desired only as an intermediate product as, for example, when the salt is formed only for purposes of purification and identification, or when it is used as an intermediate in preparing a pharmaceutically acceptable salt by ion exchange procedures.

Pharmaceutically acceptable salts of the compounds useful in the practice of this invention include those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like. The corresponding acid addition salts comprise the following: hydrochloride, sulfate, phosphate, sulfamate, acetate, citrate, lactate, tartarate, methanesulfonate, ethanesulfonate, benzenesulfonate, p-toluenesulfonate, cyclohexylsulfamate and quinate, respectively.

Pharmaceutically acceptable salts of the compounds useful in the practice of this invention include those derived from the following bases: ammonia, benzathine, procaine, diethanolamine, choline, meglumine and the like.

Pharmaceutically acceptable metallic salts of the compounds are also useful in the practice of this invention, and include those derived from the following: aluminum, calcium, lithium, magnesium, potassium, sodium, zinc and the like.

The acid addition salts of the polymeric compounds of the present invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The base addition salts of the polymeric compounds of the present invention are prepared by the addition of an aqueous solution of the amine to a suspension of the polymeric compound in water and subsequent removal of the water in vacuo.

The aryl group of the alkylaryl or heteroalkyl backbone of the polymeric compounds of the present invention can comprise a mononuclear aromatic ring or polynuclear (fused) aromatic ring, for example, compounds containing up to about 3 fused rings. Examples of fused ring monomers which can be used to prepare the polymeric compounds include naphthalene and indene. Preferably, the aryl group is derived from a monomer having no more than 2 rings and most preferably the aryl group is derived from a mononuclear compound and is polysubstituted. Examples of mononuclear monomers that can be used to prepare the polymeric compounds include polysubstituted phenylene and cycloheptatriene.

The aryl group of the alkylaryl or heteroalkylaryl backbone of the polymeric compounds of the present invention can also comprise an aromatic ring which includes heteroatoms as part of the ring structure, for example, N, O and S atoms. Examples of heterocyclic aromatic monomers that can be used to prepare the polymeric compounds include polysubstituted oxazole, furan, quinoline, indene and pyridine.

The alkyl group of the alkylaryl backbone of the polymer compound can comprise 1 to about 6 carbon atoms, can be either straight or branched, unsubstituted or substituted with, for example, amino, amide or ester groups. In preferred form, the alkyl group contains 1 to about 3 carbon atoms and is straight, and in most preferred form, the alkyl group contains one carbon atom. Examples of such alkyl groups useful in the present polymerization include lower alkyl aldehydes such as formaldehydes and lower alkyl ketones such as methyl ethyl ketone. If heteroalkyl groups are used, the preferred heteroatoms are O, S and N.

The aryl group of the alkylaryl backbone of the polymeric compounds of the present invention is preferably substituted with electronegative substituents and/or negatively charged residues, for example, carboxylic acids, phosphates, sulfates, halogens, acetyl, nitro and hydroxyl. A single substituent can optionally contain more than one of the foregoing residues, for example glycolic acid, —C(OH) COOH, which contains both hydroxyl and carboxylic acid moieties. Preferred polymeric compounds include those having alkylaryl rings with substituent selected from the group consisting of —$(CH_2)_qW(CH_2)_g$halogen, —$(CH_2)_qW(CH_2)_gOR$, —$(CH_2)_qW(CH_2)_gCHO$, —$(CH_2)_qW(CH_2)_gCOOR$, —$(CH_2)_qW(CH_2)_gCONRR$, —$(CH_2)_qW(CH_2)_gNRR$, —$(CH_2)_qW(CH_2)_gNR(COR)$, —$(CH_2)_qW(CH_2)_gPO_3R_2$, —$(CH_2)_qW(CH_2)_gOPO_3R_2$, —$(CH_2)_qW(CH_2)_gSO_2OR$, —$(CH_2)_qW(CH_2)_gOSO_2OR$, —$(CH_2)_qW(CH_2)_gS(O)_vR$, and R; with R being $C_1$-$C_{12}$ alkyl or hydrogen; W being a single bond, O, $S(O)_v$, NR(COR) or NR; q and g each being independently an integer from 0 to 4; q+g being <5; and v being 0, 1 or 2. The more preferred substituents are —$(CH_2)_qW(CH_2)_gOR$, —$(CH_2)_qW(CH_2)_gCHO$, —$(CH_2)_qW(CH_2)_gCOOR$, —$(CH_2)_qW(CH_2)_gCONRR$, —$(CH_2)_qW(CH_2)_gNRR$, —$(CH_2)_qW(CH_2)_gNR(COR)$, —$(CH_2)_qW(CH_2)_gPO_3R_2$, —$(CH_2)_qW(CH_2)_gOPO_3R_2$, —$(CH_2)_qW(CH_2)_gSO_2OR$, and —$(CH_2)_qW(CH_2)_gOSO_2OR$, and the most preferred substituents are —OH, —$(CH_2)_qW(CH_2)_gCHO$, —$(CH_2)_qW(CH_2)_gCOOR$, —$(CH_2)_qW(CH_2)_gNRR$, —$(CH_2)_qW(CH_2)_gPO_3R_2$, —$(CH_2)_qW(CH_2)_gOPO_3R_2$, —$(CH_2)_qW(CH_2)_gSO_2OR$, —$(CH_2)_qW(CH_2)_gOSO_2OR$; with R being hydrogen or lower alkyl and preferably hydrogen; W being a single bond, O, S or NR; q and g each being independently an integer from 0 to 4; and q+g<5.

Examples of "substituted" aromatic monomers which can be reacted to form polymeric compounds within the scope of the present invention include mono-, di- and trihydroxybenzoic acids, hydroxyphenylalkylcarboxylic acids, hydroxyphenoxyacetic acid, hydroxyphenylalkylsulfonic acids and hydroxyphenylalkylphosphonic acids.

Preferred Classes of Compounds

There follows a description of preferred classes of polymers of the present invention. As outlined above, the biological activity of the polymers is theorized to be related to the uniformity and conformation of the predicted lo helical structure of the polymers, characteristics determined, in part, by both the chemical formula and the method of preparation. The following describes preferred classes of polymers of the present invention, organized by the size of the unit used in the final polymerization step.

Polymers Prepared Directly from Monomers

A preferred class of polymeric compounds for use in the practice of the present invention has the structure:

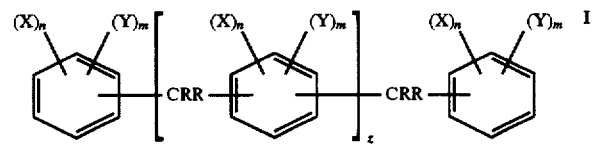

or a salt or ester thereof, wherein each X and Y is independently —$(CH_2)_qW(CH_2)_gOR$, —$(CH_2)_qW(CH_2)_gCHO$, —$(CH_2)_qW(CH_2)_gCOOR$, —$(CH_2)_qW(CH_2)_gCONRR$, —$(CH_2)_qW(CH_2)_gNRR$, —$(CH_2)_qW(CH_2)_gNR(COR)$, —$(CH_2)_qW(CH_2)_gPO_3R_2$, —$(CH_2)_qW(CH_2)_gOPO_3R_2$, —$(CH_2)_qW(CH_2)_gSO_2OR$, and —$(CH_2)_qW(CH_2)_gOSO_2OR$; R is H or lower alkyl; m and n are independently 1, 2 or 3; m+n is less than 5; Z is an integer from about 3 to about 48; W is a single bond, O, $S(O)_v$, NR(COR) or NR; v is 0, 1 or 2; q and g are each independently an integer from 0 to 4; and q+g is <5.

A particularly preferred class of polymeric compounds for use in the practice of the present invention has the structure I above, or a salt or ester thereof, wherein X is OH and Y is —$(CH_2)_qW(CH_2)_gOH$, —$(CH_2)_qW(CH_2)_gCHO$, —$(CH_2)_qW(CH_2)_gCOOH$, —$(CH_2)_qW(CH_2)_gNH_2$, —$(CH_2)_qW(CH_2)_gPO_3H_2$, —$(CH_2)_qW(CH_2)_gOPO_3H_2$, —$(CH_2)_qW(CH_2)_gSO_2OH$ or —$(CH_2)_qW(CH_2)_gOSO_2OH$; m and n are independently 1, 2 or 3; m+n is less than 5; Z is an integer from about 3 to about 48; W is a single bond, O, S or NH; q and g are each independently an integer from 0 to 4; and q+g is <5.

Speaking generally, polymeric compounds within the scope of the present invention and including as a repeating unit in the polymeric chain a single mononuclear or a single polynuclear aromatic ring structure can be prepared by polymerizing a monomeric, mononuclear or polynuclear aromatic compound with formaldehyde or other alkylaldehyde in a non-oxidizing environment in the presence of a mineral acid or organic acid. The molar ratio of the monomeric compound to the aldehyde can be within the range of about 5:1 to about 1:10, preferably, about 2:1 to about 1:3 and most preferably about 10:9. The conditions of reaction include generally the use of temperatures of about 50° C. to about 150° C. and times of about 10 minutes to about 5 hours and the use of atmospheric pressure. Such reaction will generally produce a mixture of polymers, including possibly polymeric compounds containing more than 50 and less than 5 of the aromatic ring groups. Typically, though, the product of reaction will contain predominantly polymeric compounds containing between about 5 and about 50 of the aromatic ring groups.

A desired fraction from the mixture of polymers can be separated therefrom by gel permeation chromatography.

Polymers Prepared Using Dimers

Another preferred class of polymeric compounds for use in the practice of the present invention has a repeating dimer with the structure:

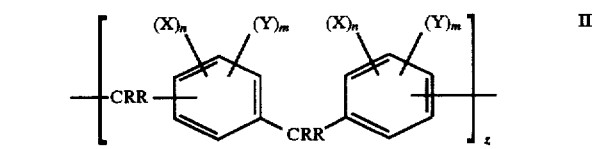

or a salt or ester thereof, wherein each X and Y is independently —$(CH_2)_qW(CH_2)_gOR$, —$(CH_2)_qW(CH_2)_gCHO$, —$(CH_2)_qW(CH_2)_gCOOR$, —$(CH_2)_qW(CH_2)_gCONRR$, —$(CH_2)_qW(CH_2)_gNRR$, —$(CH_2)_qW(CH_2)_gNR(COR)$, —$(CH_2)_qW(CH_2)_gPO_3R_2$, —$(CH_2)_qW(CH_2)_gOPO_3R_2$, —$(CH_2)_qW(CH_2)_gSO_2OR$, or —$(CH_2)_qW(CH_2)_gOSO_2OR$; R is H or lower alkyl; m and n are independently 1, 2 or 3; m+n is less than 5; W is a single bond, O, $S(O)_v$, NR(COR) or NR; v is 0, 1 or 2; q and g are each independently an integer from 0 to 4; and q+g is <5; and Z is an integer from about 1 to about 23.

Speaking generally, dimers useful in preparing polymeric compounds within the scope of this class of polymers of the present invention (including as a repeating unit in the polymeric chain a dimeric unit comprising two like-substituted aromatic rings bonded together by an alkyl or heteroalkyl bridge) can be prepared by reacting a monomeric, mononuclear or a polynuclear aromatic compound with formaldehyde or other alkylaldehyde in a non-oxidizing environment in the presence of a mineral acid or organic acid under conditions which favor the formation of a dimeric product. A method for preparing one such dimeric compound, namely, methylenedisalicylic acid, is described in Smith et al., *Anal. Chem.*, 21, No. 11, 1334 (1949). Generally, an excess of the aromatic compound is used in the reaction. The reaction is allowed to proceed for a brief time, after which the non-reacted aromatic fraction is removed, leaving an essentially homogeneous dimeric product.

The dimer can then be polymerized by reaction with formaldehyde or other alkylaldehyde in a non-oxidizing environment in the presence of a mineral acid or organic acid. The molar ratio of the dimeric compound to the aldehyde can be within the range of about 5:1 to about 1:10, and preferably, about 2:1 to about 1:3 and most preferably about 10:9. The conditions of reaction include generally the use of temperatures of about 50° C. to about 150° C. and times of about 10 minutes to about 5 hours and the use of atmospheric pressure. Such reaction will generally produce a mixture of polymers, including possibly polymeric compounds containing more than 25 and fewer than 3 of the dimeric aromatic ring groups. Typically, though, the product of reaction will contain predominantly polymeric compounds containing between about 3 and about 25 of the dimeric aromatic ring groups.

A desired fraction from the mixture of polymers can be separated therefrom by gel permeation chromatography.

Alternatively, the dimer can be polymerized by a sequential series of further dimerizations to produce, for example, tetramers, octomers, etc. By using controlled conditions, it is thus possible to produce homogenous polymers of a well-defined and predictable size. For example, dimers can be further dimerized to form tetramers; dimers and tetramers can be reacted to form hexamers; and so on.

With regard to the controlled reaction conditions which produce essentially homogenous dimers, polymers having an alkylaryl backbone can be prepared by reacting, for example, to form a diaryl alkyl dimer, an aryl anion with an aryl halide. An illustrative compound is diphenyl methane, which can be prepared by reacting a phenyl anion with a benzyl halide. The resultant dimer can itself be converted to an aryl anion by the replacement of the halide on the aromatic ring with trialkyltin. The aryl anion dimer can then be reacted with the benzyl halide dimer to produce a tetrameric compound. This process can be repeated to produce polymers having a specific degree of polymerization.

Polymers having a heteroalkylaryl backbone can also be prepared by the sequential dimerization of the base monomer. For example, a dimer consisting of a benzyl phenyl ether linkage can be prepared by reacting a phenol under neutral or basic conditions with a benzyl alcohol or benzyl halide. Subsequent removal of any protecting groups allows for the formation of the ether linkage and thus produces a tetramer consisting of two benzyl phenyl ether moieties. Protecting groups for the phenol include acetate and pivalate. Protecting groups for the benzyl alcohol include silyl ethers. The benzyl alcohol can be converted to a benzyl halide by known procedures. Heteroalkyl groups having other heteroatoms, for example, N or S, can be utilized in a similar manner. For example, phenylamine can be reacted under basic conditions with benzylbromide to produce the dimer having a methylamine linking group. Alternatively, phenylamine can be reacted with benzaldehyde under reducing condition to produce the same dimer.

Polymers Prepared from Multimers

Another preferred class of polymeric compounds for use in the practice of the present invention is closely analogous to the polymers prepared from dimers, described above, but wherein the unit used in the final polymerization step is a multimer, that is, 3 to about 8 like-substituted aromatic rings bonded together by alkyl or heteroalkyl bridges.

Speaking generally, multimers useful in preparing polymeric compounds within the scope of the present invention (including as a repeating unit in the polymeric chain a multimeric unit as described above) can be prepared by reacting a monomeric, mononuclear or a polynuclear aromatic compound with formaldehyde or other alkylaldehyde in a non-oxidizing environment in the presence of a mineral acid or organic acid under conditions which favor the formation of an oligomeric product. Generally, an excess of the aromatic compound is used in the reaction. The reaction is allowed to proceed for a brief time, after which the non-reacted aromatic fraction is removed, leaving a heterogenous multimeric product. The desired multimer from the mixture of multimers can be separated therefrom by gel permeation chromatography.

The multimer can then be polymerized by reaction with formaldehyde or other alkylaldehyde in a nonoxidizing environment in the presence of a mineral acid or organic acid. The molar ratio of the multimeric compound to the aldehyde can be within the range of about 5:1 to about 1:10, and preferably, about 2:1 to about 1:3 and most preferably about 10:9. The conditions of reaction include generally the use of temperatures of about 50° C. to about 150° C. and times of about 10 minutes to about 5 hours and the use of atmospheric pressure. Such reaction will generally produce a mixture of polymers, including possibly polymeric compounds containing more than 50 and fewer than 5 of the aromatic ring groups. Typically, though, the product of reaction will contain predominantly polymeric compounds containing between about 5 and about 50 of the aromatic ring groups.

The desired polymers from the mixture of polymers can be separated therefrom by gel permeation chromatography.

Synthesis of Specific, Homogenous Polymers

By utilizing the dimers produced by the methods described above in conjunction with the multimers produced by these methods, it is clear that polymers can be produced in a very specific manner by dimerizing various sized dimers and/or multimers as described herein. For example, a homogenous polymer of 15 units can be produced by reacting under dimerization conditions (A) a homogenous octomer produced as the product of three sequential dimerizations of the monomer and (B) a homogenous heptamer produced by the dimerization of the isolated trimer and tetramer described in this section.

It is theorized that, with regard to polymers produced directly from monomers, the polymerization of dimeric compounds results in a polymer having a more regular repeating structure, and that this type of structure may aid in the formation of a more regular helical secondary structure. Similarly, it is theorized that polymerization of multimeric compounds results in polymers having even further enhanced helical regularity, said regularity increasing with the size, in number of units, of the multimer.

As mentioned above, the backbone of the polymeric compounds of the present invention comprises about 5 to about 50 repeating aromatic units, including the end groups of the polymer. Inasmuch as the repeating units can be selected from many different types of aromatic constituents, including those which are substituted or polysubstituted and those which are mononuclear or polynuclear or those which comprise a dimer or multimer form of the aforementioned, the molecular weight of the polymeric compounds can vary over a wide range, for example, about 750 to about 10,000 Daltons, as measured by gel permeation chromatography.

Preferably, the monomers used to prepare the polymers of the present invention, and the reaction conditions used in the dimerization or multimerization, and polymerization process, are such that the resulting polymers are linear or substantially linear. The term "linear", as used herein, means a polymer having a backbone devoid of branching and/or cross-linking. Linear or substantially linear polymers are distinguished from the polymers of the aforementioned '873 application, as the polymers of the '873 application are by definition branched, that is, they comprise a repeating unit having three aryl groups, each of which is bonded to a common carbon atom.

The substituents of the aryl group can be selected to favor the formation of substantially linear polymers, that is, polymers wherein the repeating unit polymerizes primarily through only two atoms. A preferred substituent is —OR, and particularly hydroxyl, which, in terms of reactivity of the aryl group, is a strongly activating group. Moreover, hydroxyl also is a strongly directing group. For example, a hydroxyl group will greatly increase the reactivity of phenylene at the ortho and para positions. This allows the polymerization to occur under less vigorous conditions, and with greater predictability of the structure of the final product. If one of the aforementioned ortho or para positions is substituted by a second substituent, the resulting polymer will be substantially linear, as only two positions of the substituted phenol will have significant reactivity. This is especially so if the second substituent is meta-directing, for example, $-NO_2$, $-COOR$ and $-SO_3R$. A specific, and preferred, example of such a compound is salicylic acid (2-hydroxybenzoic acid), which has essentially only two sites available for polymerization, resulting in a substantially linear polymer. The substituents and position thereof on the monomers can thus be chosen to produce a polymer having specific characteristics, for example, a high degree of linearity. To this end, it is anticipated that amino groups (—NRR), which are also strongly activating and ortho, para-directing in phenylene, can be used to much the same effect as —OR. At present, however, it is anticipated that the preferred compounds will be phenolic polymers, including phenolformaldehyde type polymers.

As mentioned above, polymeric compounds within the scope of the present invention are capable of forming a helical secondary structure wherein the maximum diameter of the helical structure, as measured by the alkylaryl or heteroalkylaryl backbone, is less than 3 times greater than the maximum diameter of the aryl group of the backbone, as indicated by the computer program marketed as SYBYL® version 5.2 running on a DEC VAX® 11/750 computer. Preferably, the ratio of helix diameter:aryl diameter is between 1:1 and 2:1. Preferably, the computer-predicted helical structure comprises from about 2 to about 5 aryl groups per helical turn, most preferably from about 2 to about 3.

The aforementioned program, including dedicated hardware, is sold by Tripos Associates, Inc., a subsidiary of Evans & Sutherland, located at 1699 S. Hanley Road, Suite 303, St. Louis, Mo. 63144, and the aforementioned computer is sold by Digital Equipment Corporation, located at Marlboro, Mass. In operation, this computer program analyzes information respecting the monomeric (or dimeric) components of a polymer and calculates various characteristics of the polymer, for example, bond angles and distances, and can present a graphical image of the predicted secondary structure of the polymer. It has been observed that some of the most bioactive polymeric compounds exhibit a long, tightly-wound helical structure, with the ionic substituents oriented outward, according to the program. The program also predicts that heparin, a naturally occurring anticoagulant, has a long, tightly-wound helical structure, with the ionic substituents oriented outwardly. These two characteristics (long, tightly wound) are quantified herein by the two parameters defined above. The ratio of helix diameter to aryl diameter correlates to the length of the polymer, with smaller ratios indicating greater length, relative to width. This can be conceptualized as being analogous to stretching out a spring, which increases the length and decreases the width of the spring. By equating the thickness of the wire with the diameter of the repeating aryl group, it can be seen that the ratio of the helix diameter to aryl group diameter decreases, approaching 1:1 as the spring is stretched out. When the spring is completely stretched, the ratio is 1:1, but the structure is then linear, not helical. For any helix, therefor, the ratio of helix diameter to repeating aryl group diameter is somewhat greater than 1:1.

The number of aryl groups per helical turn correlates to how tightly the helix is wound.

As exemplary of a typical sequence of steps associated with the use of the program, the following is noted.

The first step comprises the input of information regarding the repeating unit of the polymer. Specifically, it is necessary to identify the atoms comprising the repeating unit and how the atoms are bonded together. This is the computer equivalent of drawing the molecular structure. It does not matter how the structure is drawn; once all of the atoms and bonds have been clearly identified, the computer predicts the conformation of the molecule. For polymeric compounds of the type described herein, the points of polymerization are then identified. This entails, for example, determining the nature of the reaction product of the reactants. For example, the polymer prepared from salicylic acid (2-hydroxybenzoic acid) and formaldehyde would be expected to comprise repeating 2-hydroxybenzoic acid residues linked by methylene groups at the 3- and 5- positions. Accordingly, the input includes the formula for 2-hydroxy-3-methylbenzoic acid (or 2-hydroxy-5-methylbenzoic acid) as the basic unit, with the methylene carbon and the unsubstituted 5- (or 3-) carbon of the benzoic acid ring as the points of polymerization. Finally, the degree of polymerization is entered, that is, the total number of repeating units. Upon receiving the appropriate command, the program then predicts the secondary helical structure of the compound, and generates a simulated three-dimensional graphical image of the compound on the computer monitor. This image can be rotated in any direction, magnified or shrunken, and by highlighting various parts of the polymer, quantitative information such as angles and distances can be calculated. It should be noted that the computer program is not intended to predict what products will result when the reactants are specified; the primary structure of the compound (which atoms are present, and how they are bonded together) must be given to the computer in order for the program to predict the secondary structure. Similarly, the program does not predict interactions between secondary structures, for example, helix-helix interactions, which interactions result in what are commonly known as tertiary structures.

The analytical capabilities of the computer program can more readily be understood from a consideration of the accompanying drawings. These drawings are representative of computer printouts prepared by use of the aforesaid computer program, and show the predicted secondary structure of a compound of the present invention, prepared by the polymerization of 2,4-dihydroxybenzoic acid with formaldehyde (see Example 5 hereinafter), and having the following formula.

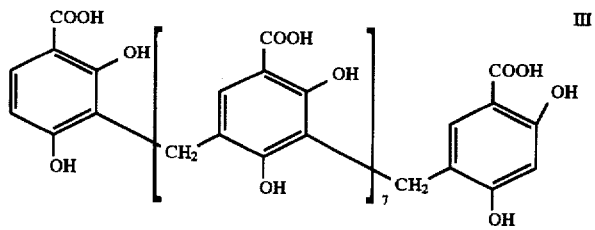

FIG. 1 views the polymer in a plane parallel to the axis of the helix. The repeating aryl groups are numbered consecutively 1–9. (The numerals were applied manually to the drawings.) Each phenylene ring has bonded thereto a carboxylic acid 12 and two hydroxyl groups 13. The resultant dihydroxybenzoic acids are bridged by methylene groups 14 to form the polymer backbone. The helix diameter, $d_h$, which is measured from the atoms of the alkylaryl backbone which are furthest apart across the width of the helix, is about 5 Å. The aryl group diameter, $d_a$, which is measured as the distance between two oppositely disposed carbons of the phenylene group, is about 2.8 Å. The ratio of helix diameter to aryl group diameter is therefore about 1.8:1, indicating a relatively long polymer.

Figure 2:
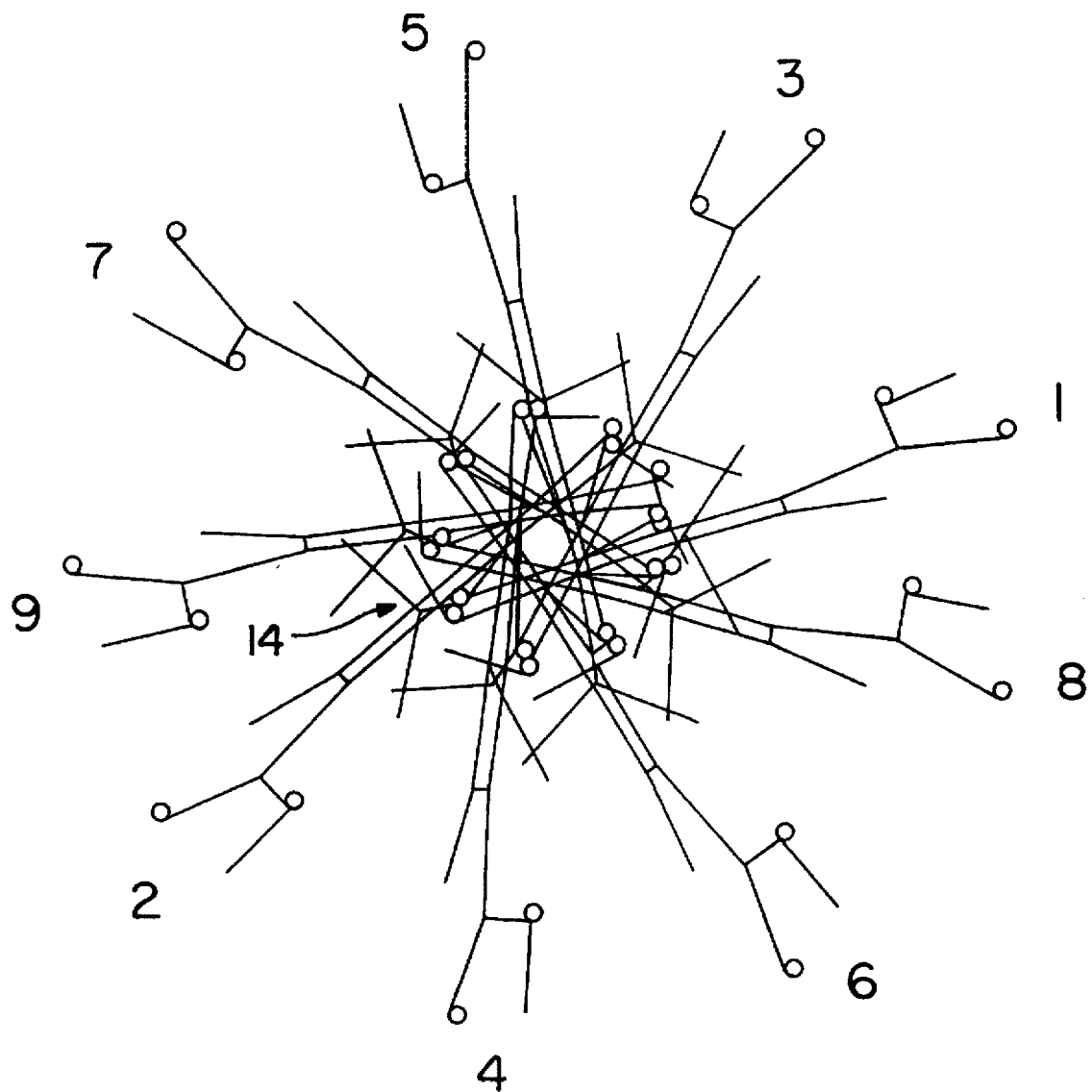
FIG. 2 is representative of a computer print of the structure shown in FIG. 1 viewed in a plane perpendicular to the helical axis.

FIG. 2 shows the computer-generated polymer in a plane perpendicular to the helical axis. The phenylene rings are numbered in the same order as for FIG. 1. A methylene bridge 14 bonds aryl groups 1 and 2. The angle between aryl groups 1 and 2 is about 160°, which translates to about 2.3 repeating units per helical turn, indicating a tightly wound helix. Heparin, a naturally-occurring glycosaminoglycan with anticoagulant activity, is also predicted by the computer program as having a long, tightly wound helix.

Pharmaceutical compositions containing the pharmacologically active polymeric compounds are believed to function according to one or more of the following mechanisms.

1. Removal of cationic proteins from the glomerular basement membrane or connective-tissues, thereby preventing local damage (i.e., via "recharging" of negatively charge residues in the glomerular basement membrane).

2. Modulation of LPL, a key enzyme in lipid distribution among various tissues which could be implicated in cardiovascular diseases.

3. Release of growth-promoting molecules, such as fibroblast growth factor (FGF), from basement membranes in order to enhance the process of angiogenesis and wound-healing. In addition, FGF can prevent death of lesioned neurons (see Anderson et al., Nature, 332, 360–1 (1988). By the release of endogenously-stored FGF, the compositions within the scope of the present invention may be useful in the treatment of neuronal disorders such as Alzheimer's disease and other dementia.

4. Blocking the activity of heparanase, an enzyme which participates in inflammatory processes and metastases formation.

5. Modulation of bone metabolism.

6. Control of the proliferation of certain cell types such as smooth muscle cells or mesangial cells.

EXAMPLES

Embodiments of the present invention are described in the following non-limiting examples which include a description of pharmacological test procedures believed to correlate to therapeutic activity in humans and other animals.

The first thirteen examples illustrate the preparation of polymeric compounds within the scope of the present invention and prepared directly from monomeric aromatic compounds. Examples 1–9 illustrate polymers prepared from mono-, di- and trihydroxybenzoic acids. Examples 10, 11 and 24 illustrate polymers prepared from mono- and dihydroxyphenylacetic acids. Example 12 illustrates a polymer prepared from dihydroxyphenylpropionic acid. Example 13 illustrates a polymer prepared from a monomer wherein a substituent group on the aryl ring contains a heteroatom, namely, hydroxyphenoxyacetic acid. Examples 14 and 15 illustrate polymers prepared from monomers wherein a substituent on the aryl ring contains more than one electronegative or negatively charged residue, namely, hydroxy and dihydroxymandelic acid. Examples 16–19 illustrate the preparation of polymeric compounds containing dimeric units and prepared using the two step process described above. Examples 20 and 21 illustrate the preparation of polymeric compounds from multimeric units, i.e., trimers and tetramers. Example 22 illustrates the preparation of a polymeric compound from a monomer which contains sulfonic acid group and Example 23 illustrates the preparation of a polymeric compound from a monomer which contains a phosphonic acid group. All of the examples utilize trioxane as the formaldehyde source. For convenience, the figures for trioxane are given in terms of weight and formaldehyde mole equivalents (mmol form. eq.).

Example 1

To 5 g (36.2 mmol) salicylic acid (2-hydroxybenzoic acid) and 1.09 g (36.3 mmol form. eq.) trioxane in 20 ml acetic acid at 90° C. was added 1 ml of 4:1 v/v acetic acid/$H_2SO_4$ (concentrated, 95–98% w/w). The reaction mixture was heated for 2 hours, cooled to room temperature, diluted with $H_2O$ and filtered. The solid product was washed with $H_2O$, dissolved in dilute $NH_4OH$ and concentrated with heat in vacuo.

Example 2

2,6-Dihydroxybenzoic acid, 2.5 g (16.2 mmol), in 10 ml acetic acid was heated at 90° C. until a clear solution was obtained. The flask was removed and 0.44 g (14.61 mmol form. eq.) trioxane was added and stirred for 2 minutes, 0.5 ml of 4:1 v/v acetic acid/$H_2SO_4$ (conc.) was added, and the solution was heated at 90° C. for 1 hour, cooled, diluted with $H_2O$ and filtered. The solid product was washed with $H_2O$, diluted with aqueous $NH_4OH$ (3:1 v/v $H_2O/NH_4OH$ (conc.) ), filtered and concentrated in vacuo ($\leq 40°$ C.).

Example 3

2,4,6-Trihydroxybenzoic acid, 2.5 g (13.3 mmol) in 10 ml acetic acid was heated at 90° C. until a solution was obtained, removed from heat, 0.36 g (11.97 mmol form. eq.) trioxane was added, stirred 2 minutes, then 0.5 ml of 4:1 v/v acetic acid/$H_2SO_4$ (conc.) was added. The reaction mixture was heated for 1 hour at 90° C., cooled to room temperature, diluted with $H_2O$, filtered, washed with $H_2O$, diluted with aqueous $NH_4OH$ (3:1 v/v $H_2O/NH_4OH$ (conc.)), filtered and concentrated in vacuo ($\leq 40°$ C.).

Example 4

Trioxane, 0.4 g (13.23 mmol form. eq.) was added to 2.5 g (14.7 mmol) 2,3,4-trihydroxybenzoic acid dissolved in 10 ml acetic acid (120° C.), the reaction mixture stirred 2 minutes and 0.5 ml of 4:1 v/v acetic acid/$H_2SO_4$ (conc.) was added. The reaction mixture was heated at 120° C. for 2 hours, cooled to room temperature, diluted with $H_2O$ and filtered. The solid product was washed with $H_2O$, dried, dissolved in dilute aqueous $NH_4OH$ and concentrated in vacuo ($\leq$40° C.).

Example 5

To a hot (90° C.) solution of 2.5 g (16.2 mmol) 2,4-dihydroxybenzoic acid in 10 ml acetic acid was added 0.44 g (14.61 mmol form. eq.) trioxane and the mixture was stirred for 2 minutes. 0.5 ml of 4:1 v/v acetic acid/$H_2SO_4$ (conc.) was added, and the reaction mixture was heated at 90° C. for 2 hours, cooled to room temperature, diluted with $H_2O$ and filtered. The solid product was washed with $H_2O$, dissolved in dilute $NH_4OH$ and concentrated in vacuo ($\leq$40° C.).

Example 6

To 4-Hydroxybenzoic acid, 2.5 g (18.1 mmol) at 90° C., was added 0.49 g (16.29 mmol form. eq.) trioxane and the reaction mixture was stirred for 2 minutes. 0.5 ml of 4:1 v/v acetic acid/$H_2SO_4$ (conc.) was added, and the reaction mixture was heated for 3 hours, cooled to room temperature, poured into $H_2O$ and filtered. The solid product was dissolved in dilute aqueous $NH_4OH$ and concentrated in vacuo ($\leq$40° C.).

Example 7

3,5-Dihydroxybenzoic acid, 2.5 g (16.2 mmol) in 14 ml acetic acid at 90° C. was added to 0.44 g (14.61 mmol form. eq.) trioxane and stirred for 5 minutes. 0.5 ml of 4:1 acetic acid/$H_2SO_4$ (conc.) was added, and the mixture was stirred for 3 hours, cooled to room temperature, diluted with $H_2O$, filtered, dissolved in dilute aqueous $NH_4OH$ and concentrated in vacuo ($\leq$40° C.).

Example 8

Trioxane, 0.44 g (14.61 mmol form. eq.), was added to 2.5 g (16.2 mmol) 3,4-dihydroxybenzoic acid in 10 ml acetic acid at 90° C., and stirred for 2 minutes. 0.5 ml of 4:1 w/w acetic acid/$H_2SO_4$ (conc.) was added, heated for 2 hours, cooled to room temperature, diluted with $H_2O$ and filtered. The solid residue was dissolved in dilute aqueous $NH_4OH$ and concentrated in vacuo ($\leq$40° C.).

Example 9

Trioxane, 0.38 g (12.72 mmol form. eq.) was added to 2.5 g (14.1 mmol) 3,5-dihydroxy-4-methylbenzoic acid in 13 ml acetic acid at 90° C., and stirred for 2 minutes. 0.5 ml 4:1 v/v acetic acid/$H_2SO_4$ (conc.) was added to the reaction mixture, heated for 2 hours, cooled to room temperature, diluted with $H_2O$ and filtered. The solid product was dissolved in dilute aqueous $NH_4OH$ and concentrated in vacuo ($\leq$45° C.).

Example 10

Trioxane, 0.44 g (14.79 mmol form. eq.) was added to 2.5 g (16.4 mmol) 4-hydroxyphenylacetic acid in 10 ml acetic acid at 90° C. 0.5 ml 4:1 v/v acetic acid/$H_2SO_4$ (conc.) was added to the reaction mixture, heated for 2 hours, cooled to room temperature, diluted with $H_2O$ and filtered. The solid product was dissolved in dilute aqueous $NH_4OH$ and concentrated in vacuo ($\leq$40° C.).

Example 11

Trioxane, 0.40 g (13.38 mmol form. eq.) was added to 2.5 g (14.9 mmol) 3,4-dihydroxyphenylacetic acid in 10 ml acetic acid at 90° C. 0.5 ml 4:1 v/v acetic acid/$H_2SO_4$ (conc.) was added to the reaction mixture, heated for 2 hours, cooled to room temperature, diluted with $H_2O$ and filtered. The solid product was dissolved in dilute aqueous $NH_4OH$ and concentrated in vacuo ($\leq$40° C.).

Example 12

Trioxane, 0.37 g (12.36 mmol form. eq.) was added to 2.5 g (13.7 mmol) 3,4-dihydroxyphenylpropionic acid in 10 ml acetic acid at 90° C. 0.5 ml 4:1 v/v acetic acid/$H_2SO_4$ (conc.) was added to the reaction mixture, heated for 2 hours, cooled to room temperature, diluted with $H_2O$ and filtered. The solid product was dissolved in dilute aqueous $NH_4OH$ and concentrated in vacuo ($\leq$40° C.).

Example 13

Trioxane, 0.40 g (13.38 mmol form. eq.) was added to 2.5 g (14.79 mmol) 4-hydroxyphenoxyacetic acid in 10 ml acetic acid at 90° C. 0.5 ml 4:1 v/v acetic acid/$H_2SO_4$ (conc.) was added to the reaction mixture, heated for 30 minutes, cooled to room temperature, diluted with $H_2O$ and filtered. The solid product was dissolved in dilute aqueous $NH_4OH$ and concentrated in vacuo ($\leq$40° C.).

Example 14

Trioxane, 0.40 g (13.38 mmol form. eq.) was added to 2.5 g (14.88 mmol) 4-hydroxymandelic acid in 10 ml acetic acid at 90° C. 0.5 ml 4:1 v/v acetic acid/$H_2SO_4$ (conc.) was added to the reaction mixture, heated for 20 minutes at 90° C., cooled to room temperature, diluted with $H_2O$ and filtered. The solid product was dissolved in dilute aqueous $NH_4OH$ and concentrated in vacuo ($\leq$40° C.).

Example 15

Trioxane, 0.15 g (4.99 mmol form. eq.) was added to 1.01 g (5.49 mmol) 3,4-dihydroxymandelic acid in 5 ml acetic acid at 90° C. 0.2 ml 4:1 v/v acetic acid/$H_2SO_4$ (conc.) was added to the reaction mixture, heated for 45 minutes, cooled to room temperature, diluted with $H_2O$ and filtered. The solid product was dissolved in dilute aqueous $NH_4OH$ and concentrated in vacuo ($\leq$45° C.).

Example 16

Step 1, formation of the dimer. Salicylic acid (2-hydroxybenzoic acid, 40 g (0.29 mol)) and 3.5 g (0.1164 mmol form. eq.) trioxane in 50 ml acetic acid were heated at 95° C. until all the salicylic acid went into solution, removed from heat and 0.5 g $H_2SO_4$ in 2.5 ml acetic acid was added. After 5 minutes, the mixture was poured into 2 L of water and stirred for about 30 minutes and filtered. The solid was diluted with 200 ml of 1:1 acetic acid/$H_2O$ and filtered, diluted with water and filtered again, washed with hot water and dried in vacuo.

Step 2, polymerization of the dimer. To 1.5 g (5.21 mol) of the resultant disalicylic acid and 0.47 g (15.63 mol form. eq.) trioxane in 10 ml acetic acid at 100° C. was added 0.5 ml of a 4:1 (v/v) acetic acid/$H_2SO_4$ solution. The reaction mixture was heated for about 4 hours, cooled to room temperature, diluted with water and filtered. The residue was diluted with dilute $NH_4OH$, concentrated on an oil bath at 90° C. and concentrated in vacuo.

Examples 17–19

Three polymers were prepared by essentially the same process as for example 16, except that the mole ratio of dimer:formaldehyde equivalent in the second step was varied as follows: example 17, 10:3; example 18, 10:9; and example 19, 1:9. For comparison, the mole ratio from example 16 was 1:3.

Example 20

Step 1, formation of trimers and tetramers. Following the procedure of Hakimalahi and Moshfegh, *Helvetica Chimica Acta*, 64, 599 (1981), methyl 4-hydroxydihydrocinnamate in methanol and concentrated $H_2SO_4$ at 0° C. was treated with the dropwise addition of formalin (35%). After the addition was complete, the mixture was stirred overnight and worked up as described by Hakimalahi and Moshfegh. Purification of the residue by silica gel chromatography using hexanes/ ethyl acetate as the eluant isolated the trimeric (methyl 3-[5-(2-methoxycarbonylethyl)-3-(5-[2-methoxycarbonylethyl]-2-hydroxybenzyl)-2-hydroxybenzyl]-4-hydroxydihydrocinnamate) and tetrameric (di[5-methoxycarbonylethyl-3-(5-[2-methoxycarbonylethyl]-2-hydroxybenzyl)-2-hydroxyphenyl]methane) products.

Step 2, polymerization of the multimers. The multimers can be polymerized essentially as described above for dimers, i.e., by treatment with trioxane and $H_2SO_4$ in hot acetic acid.

Example 21

Formation of the carboxylic acid tetramer. Di(5-hydroxycarbonyl-ethyl-3-[5-(2-hydroxycarbonylethyl)-2-hydroxybenzyl]-2-hydroxyphenyl)methane can be prepared by adding to a methanolic solution of di(5-methoxycarbonylethyl-3-[5-(2-methoxycarbonylethyl)-2-hydroxybenzyl]-2-hydroxy-phenyl]methane an excess of 1N aqueous NaOH. The mixture is stirred until all esters are hydrolyzed, acidified with concentrated HCl and extracted with $CHCl_3$ or the product filtered and dried in vacuo. The organic layer is washed with brine and dried with $MgSO_4$. Removal of the volatiles in vacuo provides the desired tetraacid.

Step 2, polymerization of the tetramer. Similar to the manner described in Example 20 above, the tetrameric phenol in hot acetic acid is treated with trioxane and concentrated $H_2SO_4$. The mixture is heated for 2 hours and worked up as described above.

Example 22

Step 1: A mixture of 4-hydroxyphenethyl alcohol (15.02 g), benzyl bromide (13.6 ml), and potassium carbonate (75.1 g) in acetone (250 ml) is heated at reflux for about 4 hours. The mixture is cooled and poured into ether and water. The organic layer is washed with water, 1N sodium hydroxide solution, brine, dried over magnesium sulfate, filtered and concentrated in vacuo to give 4-benzyloxyphenethyl alcohol.

Step 2: To a solution of 4-benzyloxyphenethyl alcohol (8.29 g) and carbon tetrabromide (24.1 g) in ether (150 ml) is portionwise added triphenylphosphine (19.0 g) and the resulting mixture stirred for about 3 hours. The supernatent is decanted, the solid washed with ether and the combined organic solution concentrated in vacuo. The crude product is purified by passing it through a silica plug to give 4-benzyloxyphenethyl bromide.

Step 3: A mixture of 4-benzyloxyphenethyl bromide (11.8 g) and sodium sulfite (8.91 g) in tert-butyl alcohol (40 ml) and water (80 ml) is heated at reflux for 40 hours, cooled to room temperature, filtered and the solid washed with water and ether to give sodium 4-benzyloxyphenethyl sulfonate.

Step 4: To a solution of sodium 4-benzyloxyphenethyl sulfonate (4.84 g) and dimethylformamide (0.5 ml) in toluene (40 ml) is added dropwise thionyl chloride (1.35 ml) and the mixture heated at 90° C. for about 5 hours. The mixture is cooled to room temperature and is added portionwise to a solution of absolute ethanol (30 ml) and pyridine (15 ml) at −20° C. The mixture is stirred for 5 hours while being allowed to warm to 0° C. The mixture is diluted with ethyl acetate and 10% aqueous hydrochloric acid. The organic layer is washed with dilute HCl, water, saturated sodium bicarbonate solution, brine, dried over magnesium sulfate, filtered and concentrated in vacuo to give ethyl 4-benzyloxyphenethyl sulfonate.

Step 5: To a solution of ethyl 4-benzyloxyphenethyl sulfonate (1.43 g) in ethyl acetate (25 ml) is added 10% palladium on carbon (0.25 g) and the mixture shaken under 30 psi of hydrogen for 3 hours. The mixture is filtered and concentrated in vacuo to give ethyl 4-hydroxyphenethyl sulfonate.

Step 6: A mixture of ethyl 4-hydroxyphenethyl sulfonate (0.42 g) in 12% aqueous hydrochloric acid (8 ml) is stirred at room temperature for about 18 hours and then heated at 100° C. for 5 hours, the concentrated in vacuo to give 4-hydroxyphenyethyl sulfonic acid.

Step 7: 4-Hydroxyphenyethyl sulfonic acid (0.34 g) and s-trioxane (0.045 g, 1.5 mmol form. eq.) are combined in acetic acid (1.5 ml) and hydrogen chloride gas bubbled into the mixture for about 10 seconds. The mixture is heated at 90° C. for 2 hours, then concentrated in vacuo. The residue is dissolved in aqueous ammonium hydroxide and the solution concentrated in vacuo to give the polymeric compound as the ammonium salt.

Example 23

Step 1: A mixture of 4-benzyloxybenzyl chloride (4.99 g) and tri-n-butylphosphite is heated at 50° C. for about 4 hours while removing butyl chloride. The mixture is cooled to room temperature and the crude product purified by HPLC on silica, eluting with 25% ethyl acetate in hexane, to give dibutyl 4-benzyloxybenzylphosphonate.

Step 2: To a solution of dibutyl 4-benzyloxybenzylphosphonate (4.07 g) in ethyl acetate (60 ml) is added 10% palladium on carbon (0.41 g) and the mixture shaken under 25 psi of hydrogen for about 20 hours. The mixture is filtered, concentrated in vacuo, and the residue purified by HPLC, eluting with a gradient of 50–65% ethyl acetate in hexane, to give dibutyl 4-hydroxybenzylphosphonate.

Step 3: A mixture of dibutyl 4-hydroxybenzylphosphonate (1.77 g) in 18% aqueous hydrochloric acid (30 ml) is heated at reflux for about 18 hours, then is concentrated in vacuo. The residue is triturated in hexanes to give 4-hydroxybenzyl phosphonic acid.

Step 4: To a mixture of 4-hydroxybenzyl phosphonic acid (0.446 g) and s-trioxane (0.0641 g, 2.1 mmol form. equiv.) in acetic acid (4 ml) at 90° C. is added a solution of saturated hydrogen chloride in acetic acid (0.5 ml) and the mixture heated at 90° C. for 2 hours. HCl gas is bubbled in briefly and heating continued for 1 hour. The mixture is concentrated in vacuo, the residue dissolved in dilute aqueous ammonium hydroxide, and this solution concentrated in vacuo to give the polymeric compound as the ammonium salt.

Example 24

A solution of 3,4-dihydroxy-6-methylphenylacetic acid (1.72 g) and s-trioxane (0.25 g) in acetic acid (5 ml) is heated to 90° C. and acetic acid/concentrated sulfuric acid (4:1) (0.25 ml) is added. The mixture is heated at 90° C. for four hours, then poured into ice water. The mixture is filtered, the solid washed with water, then dissolved in dilute aqueous ammonia. The solution is concentrated in vacuo at 40°–45° C. to give the desired product as the ammonium salt.

Activity Tests

Various of the polymeric compounds of the above examples were tested for their biological activity in processes normally associated with glycosaminoglycanprotein interaction. In these tests, the activity of the compounds tested indicates their ability to mimic glycosaminoglycans in their binding with bioactive proteins, as described earlier herein.

Inhibition of Heparinase Activity

Heparinase is an endoglucuronidase capable of degrading heparin sulfate (HS) at specific intrachain sites. Studies on degradation of sulfated proteoglycans in the subendothelial extracellular matrix (ECM) demonstrate a correlation between heparanase activity and the metastatic potential of various tumor cells. Heparinase activity is also suggested to play a role in the mobilization of normal circulating cells of the immune system during inflammatory processes.

The ability of compounds of the present invention to inhibit lymphoma-cell derived heparanase is tested in the assay system described by Vlodavsky et al., *Cancer Res.*, 43, 2704–2711 (1983). $^{35}S$ labeled ECM is incubated for 24 hours with ESb mouse lymphoma heparanase in-the presence of various concentrations of the polymers tested. Degradation of the HS is followed by gel filtration of the supernatants. Heparinase activity is expressed as the total amount of labeled low-molecular-weight fragments released from the EMC substrate. The results of this test work are summarized in Table I below.

TABLE I

| Example No. | % Inhibition of Heparinase Activity at concentration of | | | $IC_{50}$* |
|---|---|---|---|---|
| | 5 µg/ml | 10 µg/ml | 50 µg/ml | |
| 1 | 9% | 30% | 80% | 26 |
| 3 | 47% | 86% | 94% | 5.4 |
| 5 | | | | 3.7 |
| 7 | | | | 6.5 |
| 8 | | | | 4.1 |
| 10 | | | | 4.3 |
| 12 | | | | 3.0 |
| 16 | 19% | 47% | 74% | 15 |
| 18 | 33% | 63% | 83% | 7.9 |
| Heparin (control) | | | | 2.9 |

*Concentration at 50% inhibition of heparinase, as determined by linear interpolation, in µg/ml The foregoing demonstrates that the polymers of the present invention are effective inhibitors of heparanase activity, as is the commercially available glycosaminoglycan heparin.

Induction of Lipoprotein Lipase Release In-Vivo

The enzyme lipoprotein lipase (LPL) participates in the process of lipid transfer from the bloodstream to the tissues. LPL is bound to the external surface of endothelial cells via non-covalent association with cell-membrane glycosaminoglycans. Therefore, the injection of heparin results in a rapid release of LPL into the bloodstream.

In order to test for heparin-like activity, male albino rats (about 200 g) are injected with 10 mg/kg body weight of the polymers tested in saline. Blood samples are taken from the animals immediately before the injection (time 0) and 30 minutes afterwards. LPL activity is measured on duplicates of serum aliquot.

The assay system consists of 0.1 ml of serum sample and 0.1 ml of substrate containing labeled triolein, prepared according to the method of Nilsson-Ehle and Schotz, *J. Lipid Res.*, 17, 536–541 (1976). Incubations are carded out at 37° C. for 45 mins. The reaction is stopped by the addition of methanol/chloroform/heptane (1.4:1.25:1 v/v) and the extraction of fatty acids is performed according to the method of Belfrage et al., *J. Lipid Res.*, 10, 341–344 (1969), as modified by Nilsson-Ehle and Schotz. Enzyme activity is calculated according to the formula of Nilsson-Ehle and Schotz.

The results of this test work are summarized in Table II below.

TABLE II

| Example No. | Serum LPL activity (mmol FFA/hr) |
|---|---|
| Time 0 | 105 ± 39 |
| Saline (control) | 180 ± 72 |
| 1 | 188 ± 38 |
| 3 (first test) | 4111 ± 196 |
| 3 (second test) | 3324 ± 164 |
| 5 | 1586 ± 376 |
| 16 | 823 ± 139 |
| 18 | 1073 ± 223 |

The foregoing results indicate that the polymers of the present invention modulate or shift-up LPL levels, as does heparin, and that compositions within the scope of this invention may be useful in the treatment of cardiovascular diseases such as arteriosclerosis.

Anticoagulation Activity

The following demonstrates also that compounds of the present invention exhibit anticoagulant activity, as does heparin. This experiment utilizes the Activated Partial Thromboplastin Time (APTT) test, with the following procedures.

To an assay cuvette is added 100 µl of normal pooled plasma (George King Biomedical Inc., Kan.) and 100 µl of a solution containing the test compound in aqueous 50 mM Tris hydrochloride at pH 7.5 (0.2 mg of sample in one ml buffer). The sample is placed in a MLA coagulation timer which automatically maintains the sample at 37° C. for 2.5 minutes, 100 µl of actin activated cephaloplastin reagent is injected, kept 5 minutes, 100 µl of 35 mM CaCl is injected, and clot formation is determined photometrically and the clotting time recorded. Each example is examined at a variety of concentrations, generally from about 0.025 mg/ml to about 1 mg/ml, and the clotting times are graphed as a function of concentration. From the graphic results, the concentration required to double clotting time ($IC_{DCT}$) is calculated by linear interpolation. The results of this experiment are summarized in Table III below.

TABLE III

| Example No. | ID$_{DCT}$ (μg/ml) |
| --- | --- |
| 1 | >1000 |
| 2 | >500 |
| 3 | 400 |
| 4 | 650 |
| 5 | 200 |
| 6 | 400 |
| 7 | 200 |
| 8 | 125 |
| 9 | >800 |
| 10 | 150 |
| 11 | 30 |
| 12 | 50 |
| 13 | 40 |
| 14 | 100 |
| 18 | 340 |

The foregoing results indicate that the polymers of the present invention exhibit significant anticoagulant activity.

The following experiment illustrates how the anticoagulation activity of some compounds within the scope of the present invention can be affected by the use of differing proportions of the substituted aromatic compound and aldehyde in the polymerization.

The compounds examined (examples 16–19) are all produced by the two-step process described earlier, using disalicylic acid and formaldehyde (as trioxane), while varying the ratio of dimer to formaldehyde equivalent. The results of this test work are summarized in Table IV below.

TABLE IV

| Example No. | Dimer:Formaldehyde Mole Ratio | Conc. (mg/ml) | APTT (sec.) |
| --- | --- | --- | --- |
| Normal Pooled Plasma (control) | — | | ~26 |
| 19 | 1:9 | 1.0 | 27 |
| 16 | 1:3 | 1.0 | 69 |
| 18 | 10:9 | 1.0 | 115 |
| 17 | 10:3 | 1.0 | 32 |

The foregoing results indicate that the anticoagulant activity of polymers prepared from dimers varies significantly depending on the dimer:aldehyde ratio in the polymerization. As the ratio of reactants used in these types of condensations is known to have a direct effect on the degree of polymerization, this test indicates that the anticoagulant activity of the polymers is dependent on the size of the polymer. This provides a relatively simple means for controlling the degree of polymerization, and consequently, the activity of the polymers. The foregoing results, for instance, show a sharp increase in anticoagulant activity when the dimer:aldehyde mole ratio exceeds 1:9; the clotting time more than doubles between ratios of 1:9 and 1:3. At a ratio of 10:9, the activity is even higher, resulting in a more than four-fold increase in clotting time, relative to normal pooled plasma. At a ratio of 10:1, the activity is still significant, increasing clotting time by about 23%. These results indicate that, under the reacting conditions described for these examples, the polymers exhibit significant anticoagulant activity when the compounds are polymerized using a mole ratio of dimer to formaldehyde greater than about 1:9 and less than about 10:3, with particularly good activity at a ratio of about 10:9.

Inhibition of DNA Binding to Anti-DNA Antibodies

In order to study the effect of the inventive compounds on nucleic acid-protein interaction, the binding of DNA to anti-DNA mouse antibodies (MoAb) is employed as a model.

The anti-DNA A52 hybridoma antibody (IgG 2b.k) is produced by fusion of a BALB/c myeloma cell line with spleen cells of unimmunized, female NZB/NZW F1 mice as described previously (Eilat et al., *J. Immumol.*, 133, 489–494 (1984). The nitrocellulose filter assay for the binding of radiolabeled DNA to the specific antibody is performed essentially as described in Eilat et al. Briefly, reaction mixtures contains 10 μl (50 ng, 4000 cpm) of *E. coil* $^{14}$C DNA (Amersham, Buckinghamshire, England), 10 μl of medium containing A52 mouse hybridoma IgG, 10 μl of the tested inhibitor (in saline) and 0.1 ml of 0.2M borate buffered saline pH 8. In experiments designed to measure how successfully the polymers of the present invention compete with DNA in binding to DNA-specific antibodies, different concentrations of the polymers tested are mixed with radioactive DNA before adding the antibodies. The binding mixtures are left for 30 minutes at 37° C., followed by 1 hour at 4° C., then filtered through 0.45 μm nitrocellulose filters (Millipore, Bedford, Mass.). The filters are washed twice with borate buffered saline (3 ml), then dried and counted in a toluene-based scintillation liquid. The results of this test work are summarized in Table V.

TABLE V

| Example No. | IC$_{50}$ (μg/ml)* |
| --- | --- |
| 1 | 3.5 |
| 3 | 0.46 |
| 5 | 0.15 |
| 7 | 0.34 |
| 8 | 0.2 |
| 10 | 0.27 |
| 12 | 0 3 |
| 16 | 0.65 |
| 18 | 0.6 |

*Concentration at 50% inhibition of DNA binding, as determined by linear interpolation The foregoing results indicate that the aforementioned compounds compete with DNA for binding to anti-DNA antibodies. As DNA is known to be helical, this supports the computer prediction that the compounds of the present invention are helical.

Human Granulocyte Elastase Inhibition Assay

The Human Granulocyte Elastase Inhibition assay is a standard test procedure and is essentially that of Kramps, et al., "L-Pyroglutamyl-L-prolyl-L-valine-p-nitroanilide, a highly specific substrate for granulocyte elastase", *Scand. J. Clin. Lab. Invest.* 43, 427–432 (1983).

A stock solution of 8.0 mM L-pyroglutamyl-L-prolyl-L-valine-p-nitroanilide (S-2484, obtained from Kabi) in dimethylsulfoxide is diluted to 2.0 mM in 0.03M Tris buffer, pH 8.3, to give the working substrate solution. Human neutrophil elastase (obtained from ICN Biochemical) is diluted in the same buffer to 1 unit/ml to give the working enzyme solution.

A control assay is run in which a solution of 10 μl of buffer and 10 μl of working enzyme solution is incubated at room temperature for 1 minute and 330 μl of buffer and 50 μl of working substrate solution is then added. The increase in absorbance (ΔOD/min) at 405 nm is measured.

In the experimental assay 10 μl of a solution containing a polymeric compound of the present invention (in concentrations ranging from 1 mg/ml to 0.1 μg/ml), or other inhibitor to be tested, in buffer is substituted for the 10 μl of buffer with which the enzyme is incubated in the control assay and the procedure followed as for the control assay above. The ΔOD/min is measured and the result expressed as percentage inhibition for the given concentration of inhibitor as compared with the ΔOD/min for the control. Percent inhibition versus concentration of compound of the present invention or other inhibitor is plotted and the data extrapolated to give the concentration required for 50% inhibition of the enzyme ($IC_{50}$).

It has been unexpectedly found that compounds within the scope of the present invention have been found to markedly inhibit the activity of human neutrophil elastase.

Table VI below presents the results of the elastase inhibition assay in terms of $IC_{50}$ values of compounds within the scope of the present invention.

TABLE VI

| Compound of Example | $IC_{50}$ (ng/ml) |
| --- | --- |
| 13 | 130 |
| 24 | 40 |
| 22 | 205 |
| 23 | 49 |

Molecular Weight Determination of Active Fractions

The following test examines the relationship between molecular weight, and thereby degree of polymerization, and bioactivity of the polymers of the present invention. This test examines the crude product from Example 5, wherein 2,5-dihydroxybenzoic acid is polymerized with formaldehyde (as trioxane). First, the crude polymerization product, which contains different molecular weight species of the polymers of the present invention, is run through a gel permeation chromatography column, and different molecular weight fractions are collected and tested for activity using the APTT assay described earlier. Representative fractions are then examined, again with gel permeation chromatography, to determine their molecular weight ranges. The following details the procedures used.

A 2.5 cm×30 cm column containing Biogel P-6 (total volume 150 ml) is equilibrated with 50% aqueous ethanol. A sample (300 mg) of the product of Example 5, in 1–2 ml 50% aqueous ethanol is adjusted to pH 7.2 with aqueous sodium hydroxide and applied to the column. The column is eluted with 50% aqueous ethanol at a flow rate of 11 ml/hour and fractions containing 7 ml each of eluant are collected. The fractions are separately concentrated in vacuo, weighed and evaluated for anticoagulant activity using the APTT assay, at a concentration of 0.1 mg/ml. The results are shown in Table VII below.

TABLE VII

| Fraction | Weight (mg) | APTT (sec.) |
| --- | --- | --- |
| 12 | 8.6 | 42 |
| 13 | 20.9 | 44 |
| 14 | 21.9 | 45 |
| 15 | 20.6 | 42 |
| 16 | 19.0 | 40 |
| 17 | 18.1 | 41 |
| 18 | 18.3 | 34 |
| 19 | 18.2 | 32 |
| 20 | — | — |
| 21 | 16.9 | 30 |
| 22 | 10.5 | 30 |
| 23 | 14.9 | 30 |
| 24 | 10.4 | 30 |
| 25 | 8.8 | 30 |
| 26 | 6.5 | 31 |
| 27 | 5.5 | 31 |
| 28 | 5.9 | 30 |
| 29 | 4.0 | 31 |
| 30 | 2.5 | 31 |
| 31 | 5.1 | 31 |
| 32 | 1.1 | 37 |
| 33 | 1.0 | 33 |
| Normal Pooled Plasma (control) | — | 28 |

From the foregoing assay, fractions 14 and 21 are further examined, as described below, in order to determine the molecular weight of the polymers therein.

The molecular weight measurements are carried out on a Waters GPC Model IIA equipped with a Model 590 programmable solvent delivery module, a differential refractometer as detector, and an Ultrastyragel linear THF-packed column which has a tangent number of about 13,000 plates per column with an acetone marker. 2.0+0.1 mg of fractions 14 and 21 above are dissolved in 1 ml tetrahydrofuran (THF, HPLC grade from Aldrich) and filtered through a 0.5 μm teflon filter under pressure. Temperatures of both the GPC column and the detector are maintained at 35° C. THF is used as a carrier with a flow rate of 1.0 ml/min.

The molecular weight of each fraction is defined herein by four parameters. These are number average, weight average, and peak molecular weights and the molecular weight distribution. The number average molecular weight ($M_N$) represents the total weight of the polymer divided by the number of molecules present. The weight average molecular weight ($M_W$) is similar to the number average, but is weighted according to the total amount (by weight) of each species present. For example, if equal numbers of molecules having molecular weights of 1000 and 10,000 are present, $M_N$ is 5500 and $M_W$ is 9182. If equal parts by weight of molecules having molecular weights of 1000 and 10,000 are present, $M_N$ is 1818 and $M_W$ is 5500. The peak molecular weight ($M_P$) is the molecular weight species present in the highest concentration, that is, the statistical mode. The molecular weight distribution is $M_W/M_N$. The results of the gel permeation chromatograms of fractions 14 and 21, based on a monodispersed polystyrene calibration, are shown in Table VIII below.

TABLE VIII

| Fraction | $M_N$ | $M_W$ | $M_W/M_N$ | $M_P$ |
| --- | --- | --- | --- | --- |
| 14 | 1170 | 3000 | 2.56 | 1300 |
| 21 | 1080 | 2350 | 2.18 | 1000 |

The foregoing demonstrates that the anticoagulation activity of the polymers of the present invention is somewhat dependent on the molecular weight, and consequently, the degree of polymerization, of the polymer. It is clear from the above data that the anticoagulant activity of Example 5 is provided primarily by the higher molecular weight species. The above data cannot be used to precisely determine the degree of polymerization of the compounds, however, because the molecular weight determinations are based on a polystyrene calibration. Polystyrene, being nonpolar, has a chromatographic pattern different from that of the inventive polymers, which are highly polar. It is theorized, however, that the peak activity of the polymers of the present invention occurs in those polymers having a degree of polymerization of between about 5 and about 50.

Correlation of Predicted Helical Structure to Activity

Two polymers were prepared which were structural isomers of the compound depicted in FIG. 1 and described in Example 5. While FIG. 1 shows a polymer having the monomers linked in a meta orientation (1,3-), the isomers were linked in ortho (1,2-) and para (1,4-) orientations, respectively. The computer analysis predicted both the meta and para polymers to have tightly wound helical structures as defined herein, that is, with the helix diameter less than three times the aryl diameter, and with between 2 and 3 aryl groups per helical turn. Both compounds showed significant biological activity. In contrast, the ortho polymer was predicted to have a loosely wound helix, with a helical diameter greater than three times the width of the aryl group, and with about 8 to about 9 aryl groups per helical turn. Accordingly, this polymer was not significantly biologically active.

Compositions of the present invention are capable of being administered orally to produce an anticoagulant effect. In contrast, heparin can only be administered by injection.

Compositions of the present invention are useful in the treatment of cardiovascular diseases, including arteriosclerosis, bone metabolism and neuronal disorders.

Compositions of this invention can be normally administered orally or parenterally, in the treatment of cardiovascular disorders, bone metabolic disorders and neuronal disorders in humans or other mammals.

Compositions of this invention may be formulated for administration in any convenient way, and the invention includes within its scope pharmaceutical compositions containing at least one polymeric compound as described hereinabove adapted for use in human or veterinary medicine. Such compositions may be formulated in a conventional manner using one or more pharmaceutically acceptable carders or excipients. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of therapeutically effective compound to carrier are determined by the solubility and chemical properties of the compounds, the particular mode of administration and standard pharmaceutical practice. For example, excipients such as lactose, sodium citrate, calcium carbonate and dicalcium phosphate and various disintegratants such as starch, alginic acid and certain complex silicates, together with lubricating agents such as magnesium stearate, sodium lauryl, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration such as intramuscular and subcutaneous injection, solutions or suspensions of the polymeric compounds in sesame or peanut oil or aqueous propylene glycol solutions, as well as sterile aqueous solutions can be employed. The aqueous solutions using pure distilled water are also useful for intravenous injection purposes, provided that their pH is properly adjusted, suitably buffered, made isotonic with sufficient saline or glucose and sterilized by heating or by microfiltration.

The dosage regimen in carrying out the methods of this invention is that which insures maximum therapeutic response until improvement is obtained and thereafter the minimum effective level which gives relief. Thus, in general, the dosages are those that are therapeutically effective in increasing the clotting time of blood, decreasing the chances of thrombosis, reducing the buildup of arterial plaque or in the treatment of bone metabolic or neuronal disorders such as Alzheimer's disease. In general, the oral dose may be between about 3 mg/kg and about 1000 mg/kg (preferably in the range of 10 to 300 mg/kg), and the i.v. dose about 0.1 mg/kg to about 10 mg/kg (preferably in the range of about 0.5 to about 5 mg/kg), bearing in mind, of course, that in selecting the appropriate dosage in any specific case, consideration must be given to the patient's weight, general health, age and other factors which may influence response to the drug. The drug may be administered as frequently as is necessary to achieve and sustain the desired therapeutic response. Some patients may respond quickly to a relatively large or small dose and require little or no maintenance dosage. On the other hand, other patients may require sustained dosing from about 1 to about 4 times a day depending on the physiological needs of the particular patient. Usually the drug may be administered orally 1 to 4 times per day. It is anticipated that many patients will require no more than about one to about two doses daily.

It is also anticipated that the present invention would be useful as an injectable dosage form which may be administered in an emergency to a patient suffering from stroke or heart attack. Such treatment may be followed by intravenous infusion of the active polymeric compound and the amount of compound infused into such a patient should be effective to achieve and maintain the desired therapeutic response.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A pharmaceutical composition comprising in admixture with a pharmaceutically acceptable carrier a biologically active polymeric compound derived from one or more aromatic monomeric compounds that contain a phenolic moiety, said polymeric compound consisting essentially of a linear backbone having about 5 to about 50 repeating aromatic ring-containing units, selected from the group consisting of alkylaryl and heteroalkylaryl units, said compound having properties which mimic the pharmacological activity of bioactive, naturally occurring polymers including glycosaminoglycans, peptides and polynucleic acids and which is present in the pharmaceutical composition in an amount effective to compete with the binding of said naturally occurring polymers to bioactive peptides or proteins or to both of said peptides and proteins, said backbone having a helical secondary structure wherein, according to the computer program marketed as SYBYL version 5.2 running on a DEC VAX 11/750 computer, the maximum diameter of the helical structure, as measured by the alkylaryl or heteroalkylaryl backbone, is less than 3 times greater than the maximum diameter of the aryl group of the alkylaryl or heteroalkylaryl backbone, wherein said aromatic ring is substituted with one or more substituents, at least one of said substituents being an electronegative or negatively charged residue other than hydroxy or oxy; and wherein said electronegative or negatively charged residue other than hydroxy or oxy is bonded to said aromatic ring through the linking group —CRH—, wherein R is H or lower alkyl.

2. A composition according to claim 1 wherein said compound includes also an hydroxy or oxy substituent which is bonded to said aromatic ring through a linking group or is bonded directly to said aromatic ring.

3. A composition according to claim 2 wherein said aromatic ring is substituted with more than one hydroxy or oxy substituent.

4. A biologically active polymeric compound consisting essentially of a linear backbone having about 5 to about 50 repeating aromatic ring-containing units selected from the group consisting of alkylaryl and heteroalkylaryl units, said backbone having a helical secondary structure wherein, according to the computer program marketed as SYBYL version 5.2 running on a DEC VAX 11/750 computer, the maximum diameter of the helical structure, as measured by the alkylaryl or heteroalkylaryl backbone, is less than 3 times greater than the maximum diameter of the aryl group of the alkylaryl or heteroalkylaryl backbone, said compound comprising repeating units selected from

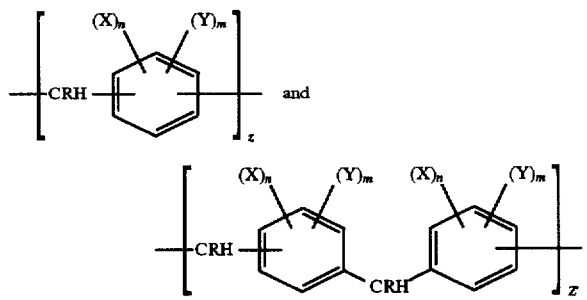

or a salt or ester thereof wherein m and n are each 1, 2, or 3, Z is an integer from about 3 to about 48, Z' is an integer from about 1 to about 23, each X and Y is independently R or a substituent selected from the group consisting of —$(CH_2)_qW(CH_2)_gOR$, —$(CH_2)_qW(CH_2)_gCHO$, —$(CH_2)_qW(CH_2)_gCOOR$, —$(CH_2)_qW(CH_2)_gCONRR$, —$(CH_2)_qW(CH_2)_gNRR$, —$(CH_2)_qW(CH_2)_gNR(COR)$, —$(CH_2)_qW(CH_2)_gPO_3R_2$, —$(CH_2)_qW(CH_2)_gOPO_3R_2$, —$(CH_2)_qW(CH_2)_gSO_2OR$, and —$(CH_2)_qW(CH_2)_gOSO_2OR$, wherein R is $C_1$–$C_{12}$ alkyl or hydrogen; W is a single bond, O, S(O)$_v$, NR(COR) or NR; q and g are each an integer from 1 to 4; and each v is independently 0, 1 or 2, with the provisos that: (a) each of the sum of m and n and the sum of q and g is independently equal to an integer which is less than 5; (b) at least one of said substituents is other than R and —$(CH_2)_qW(CH_2)_gOR$; and (c) when said substituent is —$(CH_2)_qW(CH_2)_gOR$ and R is hydrogen or methyl, q and g are each an integer from 0 to 4.

5. A compound according to claim 4 comprising from about 3 to about 25 repeating dimeric aromatic ring-containing units.

6. A compound according to claim 5 having the structure

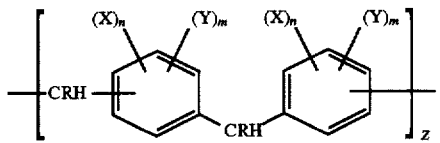

or a salt or ester thereof, wherein each X and Y is independently R or a substituent selected from the group consisting of —$(CH_2)_qW(CH_2)_gOR$, —$(CH_2)_qW(CH_2)_gCHO$, —$(CH_2)_qW(CH_2)_gCOOR$, —$(CH_2)_qW(CH_2)_gCONRR$, —$(CH_2)_qW(CH_2)_gNRR$, —$(CH_2)_qW(CH_2)_gNR(COR)$, —$(CH_2)_qW(CH_2)_gPO_3R_2$, —$(CH_2)_qW(CH_2)_gOPO_3R_2$, —$(CH_2)_qW(CH_2)_gSO_2OR$, and —$(CH_2)_qW(CH_2)_gOSO_2OR$; R is H or lower alkyl; m and n are each 1, 2 or 3; W is a single bond, O, S(O)$_v$, NR(COR) or NR; v is 0, 1 or 2; q and g are each an integer from 1 to 4; and Z is an integer from about 1 to about 23, with the provisos that (a) the sum of m and n and the sum of q and g are independently equal to an integer which is less than 5; (b) at least one of said substituents is other than R and —$(CH_2)_qW(CH_2)_gOR$; and (c) when said substituent is —$(CH_2)_qW(CH_2)_gOR$, and R is hydrogen or methyl, q and g are each an integer from 0 to 4.

7. A compound according to claim 6, wherein X is OH and Y is selected from the group consisting of —$(CH_2)_qW(CH_2)_gOH$, —$(CH_2)_q(CH_2)_gCHO$, —$(CH_2)_q(CH_2)_gCOOH$, —$(CH_2)_qW(CH_2)_gNH_2$, —$(CH_2)_qW(CH_2)_gPO_3H_2$, —$(CH_2)_q(CH_2)_gOPO_3H_2$, —$(CH_2)_qW(CH_2)_gSO_2OH$ and —$(CH_2)_qW(CH_2)_gOSO_2OH$; and W is a single bond, O, S or NH.

8. A compound according to claim 6 wherein the phenyl rings of each of the repeating dimeric units are substituted with the same substituents.

9. A mixture comprising polymeric compounds according to claim 5 and prepared by reacting a dimerized mononuclear or polynuclear aromatic compound with an alkylaldehyde in a nonoxidizing environment.

10. A process for preparing a polymeric compound according to claim 5 comprising reacting at about 50° C. to about 150° C. and for about 10 minutes to about 5 hours a dimerized form of an aromatic ring compound with an alkylaldehyde to provide said polymeric compound.

11. A process according to claim 10 including first forming a dimer of said aromatic ring compound by reacting in a non-oxidizing environment a molar excess of the aromatic ring compound with an alkylaldehyde to form said dimer.

12. A process according to claim 11 further comprising isolating said dimer prior to forming said polymeric compound.

13. A process according to claim 10 wherein said reaction is conducted at a temperature of about 50° C. to about 150° C. and for a period of time of about 10 minutes to about 5 hours.

14. A method for producing homogeneously the polymer of claim 5, wherein said polymer has a defined size, comprising a series of sequential, reaction dimerizations, said dimerizations comprising reacting an aromatic ring-containing monomeric unit with a lower alkyl aldehyde or lower alkyl ketone.

15. A method according to claim 14 further including the step of isolating the dimeric product of each dimerization.

16. A method according to claim 15 comprising three sequential dimerizations.

17. A method according to claim 15 comprising four sequential dimerizations.

18. A compound according to claim 5 wherein said ring-containing units are substituted with the same substituents.

19. A compound according to claim 4 comprising repeating multimeric units.

20. A compound according to claim 19 wherein said ring-containing units are substituted with the same substituents.

21. A compound according to claim 4, wherein said substituents are selected from the group consisting of —$(CH_2)_qW(CH_2)_gOR$, —$(CH_2)_qW(CH_2)_gCHO$, —$(CH_2)_qW(CH_2)_gCOOR$, —$(CH_2)_qW(CH_2)_gCONRR$, —$(CH_2)_qW(CH_2)_gNRR$, —$(CH_2)_qW(CH_2)_gNR(COR)$, —$(CH_2)_qW(CH_2)_gPO_3R_2$, —$(CH_2)_qW(CH_2)_gOPO_3R_2$, —$(CH_2)_qW(CH_2)_gSO_2OR$ and —$(CH_2)_qW(CH_2)_gOSO_2OR$.

22. A compound according to claim 21, wherein said substituents are selected from the group consisting of —OH, $(CH_2)_qW(CH_2)_gCHO$, —$(CH_2)_qW(CH_2)_gCOOR$, —$(CH_2)_qW(CH_2)_gNRR$, —$(CH_2)_qW(CH_2)_gPO_3R_2$, —$(CH_2)_qW(CH_2)_gOPO_3OR_2$, —$(CH_2)_qW(CH_2)_gSO_2OR$, and —$(CH_2)_qW(CH_2)_gOSO_2OR$; and R is hydrogen or lower alkyl.

23. A compound according to claim 4 having the structure

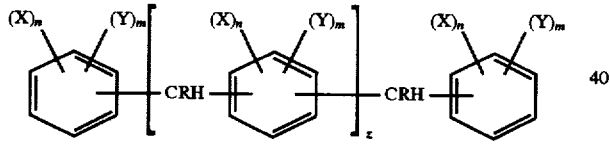

or a salt or ester thereof, wherein each X and Y is independently R or a substituent selected from the group consisting of —$(CH_2)_qW(CH_2)_gOR$, —$(CH_2)_qW(CH_2)_gCHO$, —$(CH_2)_qW(CH_2)_gCOOR$, —$(CH_2)_qW(CH_2)_gCONRR$, —$(CH_2)_qW(CH_2)_gNRR$, —$(CH_2)_qW(CH_2)_gNR(COR)$, —$(CH_2)_qW(CH_2)_gPO_3R_2$, —$(CH_2)_qW(CH_2)_gOPO_3R_2$, —$(CH_2)_qW(CH_2)_gSO_2OR$, and —$(CH_2)_qW(CH_2)_gOSO_2OR$; R is H or lower alkyl; m and n are each 1, 2 or 3; Z is an integer from about 3 to about 48; W is a single bond, O, S(O)$_v$, NR(COR) or NR; v is 0, 1 or 2; and q and g are each an integer from 1 to 4, with the provisos that (a) the sum of m and n and the sum of q and g are independently equal to an integer which is less than 5; (b) at least one of said substituents is other than R and —$(CH_2)_qW(CH_2)_gOR$; and (c) when said substituent is —$(CH_2)_qW(CH_2)_gOR$ and R is H or $CH_3$, q and g are each an integer from 0 to 4.

24. A compound according to claim 23, wherein X is OH and Y is —$(CH_2)_qW(CH_2)_gOH$, —$(CH_2)_qW(CH_2)_gCHO$, —$(CH_2)_qW(CH_2)_gCOOH$, —$(CH_2)_qW(CH_2)_gNH_2$, —$(CH_2)_qW(CH_2)_gPO_3H_2$, —$(CH_2)_qW(CH_2)_gOPO_3H_2$, —$(CH_2)_qW(CH_2)_gSO_2OH$ or —$(CH_2)_qW(CH_2)_gOSO_2OH$; and W is a single bond, O, S or NH.

25. A compound according to claim 24 having the formula

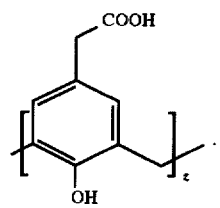

26. A compound according to claim 24 having the formula

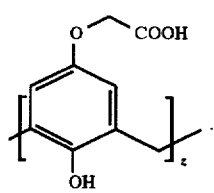

27. A compound according to claim 24 having the formula

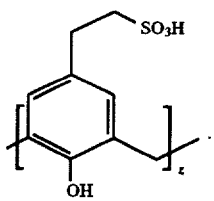

28. A compound according to claim 23 having the formula

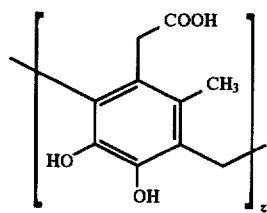

29. A compound according to claim 23 having the formula

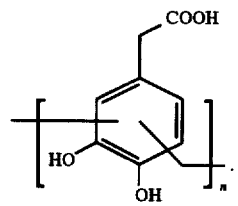

30. A compound according to claim 23 having the formula

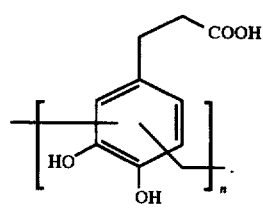

31. A compound according to claim 23 having the formula

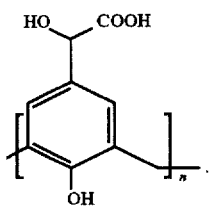

32. A compound according to claim 23 having the formula

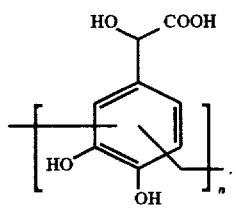

33. A mixture comprising at least two polymeric compounds according to claim 4, each having been prepared by reacting a mononuclear or polynuclear aromatic compound with an alkylaldehyde in a nonoxidizing environment.

34. A pharmaceutical composition comprising in admixture with a pharmaceutically acceptable carrier a mixture of polymeric compounds according to claim 33, said compounds having properties which mimic the pharmacological activity of bioactive, naturally occurring polymers including glycosaminoglycans, peptides and polynucleic acids and which are present in the pharmaceutical composition in an amount effective to compete with the binding of said naturally occurring polymers to bioactive peptides or proteins or to both of said peptides and proteins.

35. A pharmaceutical composition comprising in admixture with a pharmaceutically acceptable carrier a polymeric compound according to claim 4, said compound having properties which mimic the pharmacological activity of bioactive, naturally occurring polymers selected from the group consisting of glycosaminoglycans, peptides and polynucleic acids, and which polymeric compound is present in the pharmaceutical composition in an amount effective to compete with the binding of said naturally occurring polymers to bioactive peptides or proteins or to both of said peptides and proteins.

36. A pharmaceutical composition according to claim 35 wherein said polymeric compound has anticoagulant properties.

37. A pharmaceutical composition according to claim 35 capable of being administered orally.

38. A pharmaceutical composition according to claim 35 wherein said polymeric compound is capable of being absorbed into the bloodstream from the gastrointestinal tract.

39. A method of treating cardiovascular disorders comprising the administration to a human or other animal in need of such treatment a pharmaceutical composition according to claim 35 in an amount effective to treat said cardiovascular disorder.

40. A method of treating metabolic disorders of bone tissue comprising the administration to a human or other animal in need of such treatment a pharmaceutical composition according to claim 35 in an amount effective to treat said metabolic disorder.

41. A method of treating neuronal disorders comprising the administration to a human or other animal in need of such treatment a pharmaceutical composition according to claim 35 in an amount effective to treat said neuronal disorder.

42. A method for the prevention and treatment of an elastase-mediated connective tissue degradation disorder comprising the administration to a human or other animal patient in need of such therapy of a pharmaceutical composition of claim 35 in an effective elastase-inhibiting amount.

43. A compound according to claim 4 wherein said backbone comprises a heteroalkylaryl backbone.

44. A compound according to claim 43 wherein the heteroatom is selected from the group consisting of O, N and S.

45. A compound according to claim 44 wherein said heteroalkyl group is methoxy.

46. A compound according to claim 4 wherein said aromatic ring is substituted with more than one hydroxy or oxy substituent.

* * * * *